(12) United States Patent
Lau

(10) Patent No.: US 9,561,002 B2
(45) Date of Patent: Feb. 7, 2017

(54) SYSTEMS FOR MONITORING INFANT ORAL MOTOR KINETICS DURING NUTRITIVE AND NON-NUTRITIVE FEEDING

(71) Applicant: Chantal Lau, Santa Fe, NM (US)

(72) Inventor: Chantal Lau, Santa Fe, NM (US)

(*) Notice: Subject to any disclaimer, the term of this patent is extended or adjusted under 35 U.S.C. 154(b) by 0 days.

(21) Appl. No.: 14/416,039

(22) PCT Filed: Jul. 18, 2013

(86) PCT No.: PCT/US2013/051148
§ 371 (c)(1),
(2) Date: Jan. 20, 2015

(87) PCT Pub. No.: WO2014/015180
PCT Pub. Date: Jan. 23, 2014

(65) Prior Publication Data
US 2015/0196247 A1   Jul. 16, 2015

Related U.S. Application Data

(60) Provisional application No. 61/673,076, filed on Jul. 18, 2012.

(51) Int. Cl.
*A61B 5/00*   (2006.01)
*G06F 19/00*   (2011.01)
(Continued)

(52) U.S. Cl.
CPC ........... *A61B 5/4205* (2013.01); *A61B 5/0002* (2013.01); *A61B 5/0205* (2013.01); *A61B 5/038* (2013.01);
(Continued)

(58) Field of Classification Search
None
See application file for complete search history.

(56) References Cited

U.S. PATENT DOCUMENTS 3,220,382 A  *  11/1965  Carpenter ................ A01K 9/00
119/417
4,232,687 A     11/1980  Anderson-Shanklin et al.
(Continued)

FOREIGN PATENT DOCUMENTS

WO        2008/076230        6/2008

OTHER PUBLICATIONS

Niikawa, T et al. "Measurement of pressure distribution by the tongue of infants on an artificial nipple"; J. Vander Sloten, P. Verdonck, M. Nyssen, J. Haueisen (Eds.): ECIFMBE 2008, IFMBE Proceedings 22, pp. 1149-1152, 2008.*

(Continued)

*Primary Examiner* — William Thomson
*Assistant Examiner* — Marie Archer
(74) *Attorney, Agent, or Firm* — Janeen Vilven; Peacock Myers, P.C.

(57) ABSTRACT

The present invention relates to a system device and method for monitoring infant oral motor kinetics (OMK), which can be used to assess the functional significance of the different sucking components, i.e., the plasticity of infant sucking skills in relation to their oral feeding performance, at a particular time, during the developmental period and/or during preventive or therapeutic intervention programs. It is a unique system and apparatus that provides a means to study the nonnutritive and/or nutritive sucking skills, i.e., the Suction and/or Expression components of sucking, of infants in the natural setting, i.e., during a normal feeding session. OMK sensors, tracked in real-time by the monitoring system, include miniature pressure transducers, or pressure sensitive pads, attached to the nipple for measuring intraoral pressure pulses during Suction, and for measuring compression/stripping pressure pulses during Expression; and a miniature flow sensor for measuring fluid flow rate, (Continued)

which can be integrated over time to determine the volume of milk removed (bolus) per suck. Other signals, such as respiration, swallowing, thermal, optical, and acoustic signals can be recorded and compared along with the instrumented-nipple signals, in an OMK monitoring system.

23 Claims, 32 Drawing Sheets

(51) Int. Cl.
    *A61J 11/00*         (2006.01)
    *A61B 5/11*          (2006.01)
    *A61B 5/22*          (2006.01)
    *A61B 5/03*          (2006.01)
    *G01F 1/34*          (2006.01)
    *G01F 1/36*          (2006.01)
    *G01F 1/42*          (2006.01)
    *G01F 15/06*        (2006.01)
    *A61B 5/0205*      (2006.01)
    *A61B 5/145*        (2006.01)
    *A61J 13/00*        (2006.01)
    *A61J 17/00*        (2006.01)
    *A61J 9/00*         (2006.01)
    *A61B 5/024*       (2006.01)
    *A61B 5/08*         (2006.01)
    *A61J 7/00*         (2006.01)

(52) U.S. Cl.
CPC ......... *A61B 5/1107* (2013.01); *A61B 5/14542* (2013.01); *A61B 5/224* (2013.01); *A61B 5/4233* (2013.01); *A61B 5/4552* (2013.01); *A61B 5/6806* (2013.01); *A61B 5/6887* (2013.01); *A61B 5/72* (2013.01); *A61B 5/742* (2013.01); *A61J 11/00* (2013.01); *A61J 13/00* (2013.01); *A61J 17/00* (2013.01); *G01F 1/34* (2013.01); *G01F 1/363* (2013.01); *G01F 1/42* (2013.01); *G01F 15/063* (2013.01); *G06F 19/34* (2013.01); *A61B 5/024* (2013.01); *A61B 5/08* (2013.01); *A61B 2503/04* (2013.01); *A61B 2503/045* (2013.01); *A61B 2560/0475* (2013.01); *A61B 2562/0247* (2013.01); *A61J 7/0053* (2013.01); *A61J 9/00* (2013.01); *A61J 17/001* (2015.05); *A61J 17/003* (2015.05); *A61J 17/006* (2015.05); *A61J 2200/76* (2013.01)

(56) References Cited

U.S. PATENT DOCUMENTS

| | | | | |
|---|---|---|---|---|
| 6,511,441 | B1* | 1/2003 | Wakumoto | A61B 5/228 600/561 |
| 6,702,765 | B2* | 3/2004 | Robbins | A61B 5/228 600/590 |
| 7,540,388 | B2 | 6/2009 | Silver | |
| 2006/0074354 | A1 | 4/2006 | Barlow et al. | |
| 2008/0039778 | A1* | 2/2008 | Goldie | A61B 5/038 604/67 |
| 2008/0183107 | A1* | 7/2008 | Miller | A61B 5/228 600/590 |
| 2009/0156967 | A1 | 6/2009 | Cohen | |
| 2012/0302924 | A1* | 11/2012 | Cunningham | A61B 5/038 600/590 |
| 2014/0207024 | A1* | 7/2014 | Aron | A61B 5/4542 600/590 |
| 2014/0242213 | A1* | 8/2014 | McCarty | A61J 9/00 426/2 |
| 2014/0296661 | A1* | 10/2014 | Zwartkruis-Pelgrim | A61B 5/228 600/301 |

OTHER PUBLICATIONS

Lau, C. et al.; "Quantitative Evaluation of Infant's Nonnutritive and Nutritive Sucking"; Dysphagia 16:58-67 (2001).*
Cooper, B. "Changes in Nutritive Sucking Patterns with Increasing Gestational Age"; Nursing Research; vol. 40; No. 4, Jul./Aug. 1991; p. 245-247.*
Geddes, D. T.; "Tongue movement and intra-oral vacuum in breastfeeding infants"; Early Human Development (2008) 84, 471-477.*
Lau, C. et al; "Oral feeding in Low Birth weight infants"; J. Pediatr. (1997); 130:561-9.*
Lau, C. et al; "Characterization of the developmental stages of sucking in preterm infants during bottle feeding"; Acta Paediatr. (2000); 89:846-52.*
Lau, C. et al; "Coordination of suck-swallow and swallow respiration in preterm infants"; Acta Paediatr. (2003); 92:721-727.*
Lau, C. et al; "Maturation of oral feeding skills in preterm infants"; Acta Paediatr. (2008); 92; 61-67.*
Niikawa, T. et al; "Measurement of Tongue-Artificial nipple contact pressure during infant sucking"; IEEJ Trans 2012; 7; 190-196.*
Oommen, P. M. "Breathing patterns of preterm infants during bottle feeding: Role of milk flow"; The Journal of Pediatrics; (1991); vol. 119; No. 6; p. 961-965.*
Amaizu, et al., "Maturation of oral feeding skills in preterm infants", Acta Pædiatrica vol. 97, 2008, 61-67.
Ardran, et al., "A Cineradiographic Study of Bottle Feeding", The British Journal of Radiology, vol. 31, Issue 361, 1956, 11-22.
Ardran, et al., "A Cineradiographic Study of Breast Feeding", The British Journal of Radiology, vol. 31, Issue 363, 1958, 156-162.
Daniels, et al., "Mechanisms of Feeding Efficiency in Preterm Infants", Journal of Pediatric Gastroenterology and Nutrition, vol. 5, 1986, 593-596.
Demonterice, et al., "Concurrent valliditiy of a new instrument for measuring nutritive sucking in preterm infants", Nurs Res., vol. 41, No. 6, 1992, 342-346.
Dubignon, et al., "Sucking in the newborn during a feed", Journal of Experimental Child Psychology, vol. 7, Issue 2, 1969, 282-298.
Fucile, et al., "A Controlled-flow Vacuum-free Bottle System Enhances Preterm Infants' Nutritive Sucking Skills", Dysphagia, vol. 24, 2009, 145-151.
Fucile, "Effect of an oral stimulation program on sucking skill maturation of preterm infants", Developmental Medicine & Child Neurology, vol. 47, 2005, 158-162.
Fucile, et al., "Oral and non-oral sensorimotor interventions enhance oral feeding performance in preterm infants", Dev Med Child Neurol., vol. 53, No. 9, 2011, 829-835.
Fucile, et al., "Oral and Nonoral Sensorimotor Interventions Facilitate Suck-Swallow-Respiration Functions and Their coordination in Preterm Infants", Early Hum Dev., vol. 88, No. 6, 2012, 345-350.
Fucile, et al., "Oral stimulation accelerates the transition from tube to oral feeding in preterm infants", The Journal of Pediatrics, vol. 141, No. 2, 2002, 230-236.
Gryboski, "The Swallowing Mechanism of the Neonate I. Esophageal and Gastric Motility", Pediatrics, vol. 35, No. 3, 1965, 445-452.
Jain, et al., "Energetics and mechanics of nutritive sucking in the preterm and term neonate", The Journal of Pediatrics, vol. 111, Issue 6, Part 1, 1987, 894-898.
Kron, et al., "Consistent Individual Differences in the Nutritive Sucking Behavior of the Human Newborn", Psychosomatic Medicine, vol. 30, 1968, 151-161.
Lau, et al., "A Novel Approach to Assess Oral Feeding Skills of Preterm Infants", Neonatology, vol. 100, 2011, 64-70.
Lau, et al., "Characterization of the developmental stages of sucking in preterm infants during bottle feeding", Acta Paediatr, vol. 89, 2000, 846-852.
Lau, "Coordination of suck-swallow and swallow respiration in preterm infants", Acta Paediatr, vol. 92, 2003, 721-727.
Lau, et al., "Development of Oral Feeding Skills in the Preterm Infant", Handbook of Growth and Growth Monitoring in Health and Disease, Part 3, 2012, 499-512.
Lau, et al., "Interventions to improve the oral feeding performance of preterm infants", Acta Paediatrica, vol. 101, 2012, e269-e274.

(56) References Cited

OTHER PUBLICATIONS

Lau, "Is there an advantage for preterm infancts to feed orally in an upright or sidelying position", Journal of Neonatal Nursing, vol. 19, Issue 1, 2013, 28-32.

Lau, et al., "Oral Feeding in Infants", Cliff Probl Pediatr., vol. 29, 1999, 105-124.

Lau, et al., "Oral feeding in low birth weight infants", The Journal of Pediatrics, vol. 130, Issue 4, 1997, 561-569.

Lau, et al., "Oral feeding in premature infants: advantage of a self-paced milk flow", Acta Paediatr., vol. 89, 2000, 453-459.

Lau, et al., "Quantitative Evaluation of Infant's Nonnutritive and Nutritive Sucking", Dysphagia, vol. 16, 2001, 58-67.

Mathew, et al., "Breating pattern and ventilation during oral feeding in term newborn infants", The Journal of Pediatrics, vol. 106, Issue 5, 1985, 810-813.

Rasch, "The preterm piglet—a model in the study of oesophageal development in preterm neonates", Acta Paediatrica, vol. 99, 2010, 201-208.

Sameroff, "The components of sucking in the human newborn", Journal of Experimental Child Psychology, vol. 6, Issue 4, 1968, 607-623.

Scheel, et al., "Does the choice of bottle nipple affect the oral feeding performance of very-low-birthweight (VLBW) Infants?", Acta Paediatr., vol. 94, No. 9, 2005, 1266-1272.

Simpson, et al., "Early Introduction of Oral Feeding in Preterm Infants", Pediatrics vol. 110 No. 3, 2002, 517-522.

Tamilia, et al., "A New Ecological Method for the Estimation of Nutritive Sucking Efficiency in Newborns: Measurement Principle and Experimental Assessment", 35th Annual International Conference of the IEEE EMBS Osaka, Japan, Jul. 3-7, 2013, 2013, 6720-6723.

Tamilia, et al., "Technological Solutions and Main Indices for the Assessment of Newborns' Nutritive Sucking: A Review", Sensors, vol. 14, 2014, 634-658.

Wang, et al., "Development of Wireless Oral-feeding Monitoring System for Preterm Infants", IEEE Journal of Biomedical and Health Informatics, 2013, 1-7.

Wolff, "The Serial Organization of Sucking in the Young Infant", Pediatrics, vol. 42, No. 6, 1968, 943-956.

\* cited by examiner

A SYSTEMS FOR MONITORING INFANT ORAL MOTOR KINETICS DURING NUTRITIVE AND NON-NUTRITIVE FEEDING

CROSS-REFERENCE TO RELATED APPLICATIONS

This application claims priority to and the benefit of the filing of U.S. Provisional Patent Application No. 61/673,076, entitled Systems and Method for Monitoring Infant Oral Motor Kinetics During Nutritive and Non-Nutritive Feeding, filed on Jul. 18, 2012, and the specification and claims thereof are incorporated herein by reference.

BACKGROUND OF THE INVENTION

Field of the Invention

The present invention relates, in general, to improved systems, methods, and devices for monitoring the oral motor kinetics of an infant during nutritive sucking (NS) and non-nutritive sucking (NNS).

Introduction

As the ability of an infant/newborn to feed by mouth safely and efficiently is dependent on the proper development of his/her oral feeding skills, researchers have developed a number of systems for monitoring infant sucking. Sucking is the mechanism used by an infant to feed in order to obtain milk/nutrition. Sucking comprises two components, Suction and Expression. Suction corresponds to the generation of a negative pressure in the oral cavity (intraoral) which draws the liquid into the mouth. Expression corresponds to the generation of a positive pressure when the tongue squeezes the nipple against the hard palate which ejects the liquid into the mouth. The systems for monitoring infant sucking fall into three categories. The first category measures the number of sucks by the number of pressure changes inside the nipple/bottle (1-3). The second monitors only the Suction component of sucking (4, 5). The third system monitors both components of sucking, Suction and Expression (6-9). Suction is defined as the negative intraoral pressure exerted to draw milk from a bottle or breast into the mouth. Expression, is defined as the compression and/or lengthwise stripping of the nipple (bottle or breast) by the tongue, pushing up against the infant's hard palate to eject milk into the mouth (10, 11).

As the infant's oral motor skills develop, it has been shown that the Expression component appears first, followed by the Suction component (9). Infants using the Expression component alone can feed by mouth safely and successfully, albeit not as efficiently as when using a rhythmic alternation of Suction and Expression (8, 9); the latter being recognized as the full-term sucking pattern (6, 7, 9). These studies demonstrate the physiologic and functional importance of the Expression component of sucking. It has been speculated that compression primarily occurs with immature Expression, while stripping which also includes compression occurs with mature Expression. In brief, studies using monitoring systems that do not include both components of sucking, and in artificial settings, lead to an incomplete understanding of oral motor kinetics and feeding skills. This not only threatens the infants' safety and competence when feeding by mouth, but it also provides an inaccurate knowledge base for the development of oral feeding interventions.

Background of the Present Invention

An embodiment of the present invention measures oral motor kinetics of an infant. Both the Suction and Expression components of sucking were measured using a miniature pressure transducer for each component (total of 2 transducers), during normal oral feeding sessions (FIG. 1). The first system allowed monitoring with a standard bottle as used in nurseries, and in which infants obtained milk regardless of the sucking pattern they used, Expression alone or alternation of Suction/Expression. The individual Suction and Expression pressure traces were recorded simultaneously; and the overall oral feeding performance was characterized by evaluating two parameters, the percent of overall milk transfer [(volume taken/volume to be taken)× 100] and the rate of milk transfer over the entire feeding period (ml/min) (8). Referring now to FIG. 1, pressure transducer plates 103 are associated with the nipple of instrumented bottle 101. A soft Silastic tubing 105 provides covering for the transducer 103 when transducer 103 is partly located outside of the nipple of bottle 104. This prevents the transducer 103 from being in direct contact with infant's oral cavity. Gray shading 102 indicates fluid for delivery through the nipple. Transducer 103 may measure negative pressure (Suction) or positive pressure (compression) or both. Suction pressure signal 109 and Expression pressure signal 111 are transmitted via wires in communication with signal processor 113. The wires are located within tubing 107. The tubing may be for example PE. In one embodiment the tube 105 is connected to tube 107. However, the signal may be transmitted wirelessly also. The processed signal [−] or [+] is displayed on monitor 115. The negative pressure is detected at transducer 103 (illustrated as a dot connected to wire 112 in the lower portion of the tip of the nipple).

The stages of infant feeding were recorded. A 5-point scale (1A; 1B; 2A; 2B; 3A; 3B; 4; 5) characterizing five developmental stages of nutritive sucking during bottle feeding, beginning with the appearance of only the Expression component, followed later by that of the Suction component (FIG. 2), was validated. Immature sucking is characterized primarily by the use of Expression-alone (Stage 1, which is less efficient); while mature sucking, as seen in infants born at term gestation, is characterized by the rhythmic alternation of Suction/Expression (Stage 5, which is more efficient). A direct relationship was demonstrated to exist between these developmental stages and the oral feeding performance parameters, as defined above (9).

The understanding of the maturation process in infant sucking skills, gained with measurements from the first OMK system, has allowed the development of preventive and therapeutic interventions to assist infants with oral feeding difficulties (12-16).

BRIEF SUMMARY OF THE INVENTION

The present invention relates to systems, methods, and devices for monitoring an infant's Oral Motor Kinetics (OMK). We define the term "oral motor kinetics" as being "the changes in oral motor skills" of an infant as the infant matures. Knowledge of an infant's OMK parameters and characteristics can be used to assess the functional significance of the different sucking components, i.e., the plasticity of infant sucking skills in relation to their oral feeding performance, at a particular time, during the developmental period and/or during preventive or therapeutic intervention programs. The devices and methods of an OMK system can provide a unique means for studying the nonnutritive and nutritive sucking skills of individual infants in a natural setting, i.e., during a normal feeding session; as opposed to an artificial one, e.g. when milk is only delivered to the baby if he uses the Suction component. This is particularly of germane importance when monitoring nutritive sucking, insofar as researchers aim at gaining an understanding of the impact that such skills can have on how safely and efficiently an infant orally feeds and how best to develop efficacious interventions to enhance such performance.

OMK monitoring systems, according to an embodiment of the present invention, offer several features, all of which can benefit infants. To monitor nonnutritive sucking, monitoring sensors can be adapted onto a pacifier, or onto a disposable glove, such as routinely used by feeding therapists for the clinical evaluation of infants' sucking. To monitor nutritive sucking from bottle feeding, monitoring sensors can be adapted to any type of bottle nipples for use on any type of bottle, to a breast, or a nipple shield for breastfeeding.

When adapted for non-nutritive sucking, it will provide an accurate feedback of the developmental stage of the infants' Suction and Expression, along with their coordinated activities. Its use as a clinical evaluation tool will offer feeding therapists important information on specific measures relating to an infant's sucking, e.g., frequency of Suction and/or Expression components, respective amplitude/force (mmHg), number of Suction and Expression per sucking burst, duration of sucking burst (17).

When adapted for nutritive bottle-feeding, an OMK monitoring system can monitor the Suction and Expression component of sucking, and can also provide information on the flow rate and volume (bolus) of milk intake resulting directly from the infant's sucking skills, as would normally occur during a normal bottle feeding and not predetermined by existing patented monitoring systems. This is achieved because milk fills the nipple chamber and flow occurs regardless of whether the infant uses Suction, Expression, or a combination of both. As such, its use during bottle feeding will provide not only an exact description of the characteristics of individual infants' Suction and Expression, e.g., force/amplitude, frequency, interaction, and synchronization, but also their impact on infants' feeding performance, e.g., ability to complete a feeding session, efficiency/rate of milk transfer. Furthermore, its use over time, as infants mature, will identify their maturation process. For those with oral feeding difficulties, it will help identify potential causes of discrepancy, as well as to monitor the efficacy of any interventions provided.

OMK monitoring systems are simple to use, non-invasive, and are generally compatible with a wide variety of recording devices equipped with appropriate analytical software programs. The systems and devices can also be easily expanded to simultaneously record other physiological parameters, e.g., swallowing, respiration, esophageal activity, and clinical vital signs, e.g., oxygen saturation and heart rate. In some embodiments, various components of the monitoring system are disposable (one-time use).

OMK monitoring systems, according to some embodiments, can quantitatively monitor a variety of variables and parameters, including, but not limited to: a) infant nutritive sucking skills, b) the volume of fluid (i.e., milk) ingested during routine bottle feeding, c) their direct impact of infant's feeding efficacy, d) infant nonnutritive sucking skills, e.g., on a pacifier, and e) the individual characteristics (simultaneously) of the two components of nutritive and nonnutritive sucking: Suction and Expression. One embodiment of the OMK monitoring system allows an infant to get milk by using their true skills, e.g., Expression only, Suction only, or a combination of both Suction and Expression within a normal feeding, as provided when using a standard feeding bottle.

An embodiment of the OMK monitoring system can be used for nonnutritive (NNS) (e.g., pacifier, glove system), and/or for nutritive (NS) sucking measurements (e.g., bottle-feeding). The OMK devices and methods can distinguish between Suction and Expression, and they can also differentiate between the two different Modes of Expression, namely: 1) compression-only and 2) compression plus stripping. Some OMK devices can measure the volume of bolus per suck during nutritive sucking (which can be used as a measure of efficacy).

The various parameters that are monitored by an OMK system can provide useful information on the development of the neuromotor plasticity of the sucking function when the parameters are analyzed as a function of bolus volume.

One embodiment of the present invention provides for a system for monitoring oral motor kinetics in an infant comprising a nipple comprising a first pressure transducer and a second pressure transducer for detecting pressure when the nipple is placed in the mouth of an infant and a processor in operational communication with the first pressure transducer and the second pressure transducer of the nipple for processing a signal from the first pressure transducer and the second pressure transducer to provide information about the infant's oral motor kinetics when the nipple is in the infant's mount.

Additionally, the nipple may comprise a third pressure transducer located at a distance $L_o$ from the second pressure transducer on the nipple long axis.

The processor of this embodiment may be in operational communication with the third pressure transducer for processing a signal from the third transducer to provide information about the infant's oral motor kinetics when the nipple is in the infant's mouth.

The second pressure transducer and the third pressure transducer may be located within a tube positioned at least partially on the exterior of a neck of the nipple such that the tube would be in contact with the mouth of the infant when the nipple is in use.

Further the second pressure transducer and third pressure transducer may each be a pressure transducer measuring the positive pressure exerted by the Expression component of sucking when the tongue compresses and/or strips the nipple against the hard palate.

The first pressure transducer may be located at the distal tip of the nipple.

Additionally the second pressure transducer may be located closer to a base of the nipple as compared to the position of the third pressure transducer which is located closer to a tip of the nipple as compared to the position of the second pressure transducer.

Further still the first transducer may be a pressure transducer measuring the negative intraoral pressure exerted by the Suction component of sucking.

Additionally, the distance $L_o$ between the second pressure transducer and the third pressure transducer can be between about 0.1-3 cm along the long axis of the nipple.

Additionally the nipple may be selected from a nipple shield, a finger of a glove, a pacifier or a nipple of a feeding bottle.

In this embodiment the processing by the processor may be selected from the group consisting of receiving, storing, displaying, analyzing and transmitting.

Additionally the processor may be operatively connected to a display for displaying the signal from the first pressure transducer and the second pressure transducer.

Or further still, the processor may be operatively connected to a display for displaying the signal from the first pressure transducer the second pressure transducer and the third pressure transducer.

Additionally, the operational communication of the processor to the first pressure transducer and second pressure transducer may be wireless.

Further still the operational communication of the processor to the third pressure transducer is wireless.

Operational communication may include transmitting a signal through a conductive wire or transmitting a signal with a frequency such as infrared frequency or radio frequency or a mechanical communication such as hydraulics. Associated with the nipple includes adjoined, connected, adhered, attached permanently or releasably.

According to another embodiment, an instrumented nipple comprises a first pressure transducer and a second pressure transducer associated with the instrumented nipple for detecting pressure when the instrumented nipple is placed in the mouth of an infant wherein the first pressure transducer is located at the tip of the nipple.

Further the first transducer may be a pressure transducer measuring the negative pressure exerted by the Suction component of sucking.

Further still the second pressure transducer may be a positive pressure transducer for measuring the Expression component of sucking.

The second pressure transducer may be associated with a neck of the instrumented nipple.

Further a third pressure transducer may be located on the neck of the nipple at a distance of between about 0.1-3 cm from the second pressure transducer on the nipple's long axis wherein the third pressure transducer is a positive pressure transducer.

Another embodiment provides for a method for evaluating an infant's oral motor kinetics comprising inserting an instrumented nipple according to any one of the instrumented nipples disclosed herein into the mouth of an infant and detecting the infant's oral motor kinetics by the activation of a pressure transducer of the instrumented nipple according to any one of claims 16-20 from the pressure provided from within the infant's mouth causing activation of the pressure transducer to create a signal. The signal is received and analyzed from activation of the pressure transducer to determine the oral motor kinetics of the infant during sucking.

Additionally the step of analyzing the signal includes measuring over time the pressure at the second pressure transducer and the third pressure transducer located in the neck of the nipple to determine the mode of Expression.

Further still the oral motor kinetics is non-nutritive sucking when the nipple is a finger glove or a pacifier.

Additionally, the nipple may be a nipple attached to a feeding bottle delivering fluid to the infant during nutritive sucking.

Further still the nipple may be a nipple shield placed on a breast delivering milk to the infant during breastfeeding.

Further still the instrumented nipple of can measure a characteristic of sucking selected from the group consisting of the duration of the sucking action, the amplitude/force (mmHg) of the Suction and Expression components of the sucking action and the number of Suction and Expression per sucking burst.

The method embodiment may further comprise analyzing the Expression component with the instrumented nipple to identify compression and/or stripping signals or may further comprise monitoring the amount of fluid delivered to the infant from the nipple or may further comprise monitoring a clinical parameter selected from the group consisting of heart rate, oxygen saturation, respiration, and esophageal activity.

Another embodiment of the present invention provides for an instrumented nipple for measuring infant feeding performance comprising a nipple having a tip, and a base connected via a neck wherein the tip contains an nipple exit hole through which fluid exits when the base of the nipple is securely connected to a bottle of fluid wherein the nipple exit hole comprises a calibrated flow orifice insert having a diameter $D_o$ and a length $L_o$ wherein a calibrated flow orifice directs all fluid exiting the nipple past a first pressure transducer and a second pressure transducer of the calibrated flow orifice to detect pressure change as the fluid passes through the calibrated flow orifice insert of the instrumented nipple.

Further still, the first pressure transducer is located at the inlet of the calibrated flow orifice or inside of the calibrated flow orifice near the inlet.

Additionally the second pressure transducer is located at the outlet of the calibrated flow orifice or inside of the calibrated flow orifice near the outlet.

Alternatively the first transducer and the second transducer are embedded in the sidewall of the orifice.

Further still the calibrated flow orifice remains unchanged in shape during sucking.

Further still the calibrated flow orifice may further comprises an internal flange with a large diameter that fits within the nipple at the nipple tip to prevent the calibrated flow orifice insert from exiting the nipple exit hole.

Another embodiment of the present invention provides a method of measuring infant feeding performance comprising measuring the fluid flow rate of fluid to an infant delivered with an instrumented according to an embodiment of the present invention wherein the difference in pressure between a first pressure transducer (P1) and a second pressure transducer (P2) is proportional to the square root of the pressure drop, $\Delta P_{1-2}=P1-P2$.

Yet another embodiment of the present invention provides for an instrumented nipple for use with an Oral Motor Kinetics (OMK) monitoring system comprising a nipple and a pressure sensitive pad attached to the nipple wherein the pressure sensitive pad comprises a two-dimensional (2-D) array of pressure sensitive elements capable of providing a plurality of real-time electrical signals representing a time.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

Embodiments of the present invention relate, in general, to improved systems, methods, and devices for monitoring the oral motor kinetics (OMK) of an infant during nutritive (NS) or non-nutritive (NNS) sucking.

Note: the term "infant" is broadly defined herein as including any infant mammal, not just human infants. Also, the term "infant" is further defined as including any age, i.e., ranging from premature infants (and mammals) to elderly people (and mammals).

One aspect of an embodiment of the present invention provides for an improved OMK monitoring system that simultaneously measures Suction and Expression forces and pressures applied to a nipple by the infant. This can be accomplished, for example, by using miniature/micro pressure transducers attached at specific locations on the nipple. For example, these can be placed flushed to the tip of the nipple, without protruding into the infant's mouth, to directly measure the Suction component of sucking, i.e. the negative intraoral pressure and also along the midsection/neck of the nipple to directly measure the Expression component of sucking, i.e. the positive compressive pressure generated by the compression and/or stripping of the nipple between the tongue and the hard palate.

Another aspect of an embodiment of the present invention is that an instrumented nipple should replicate a standard bottle (e.g., with respect to geometry, shape, texture, smoothness, symmetry, and stiffness/elasticity (durometry), with milk filling the entire chamber inside the nipple, especially when monitoring the Expression component of sucking, so that the infant's natural feeding regimen can be simulated as closely as possible.

Another aspect of an embodiment of the present invention provides an, OMK monitoring system, that when used on the same subject within the same time frame, comparing non-nutritive and nutritive sucking, can be used to determine whether an infant's oral feeding problems are due to issues with sucking, or due to some other physiological function, e.g., swallowing, breathing, upper gastrointestinal function, etc.

Figure 3:
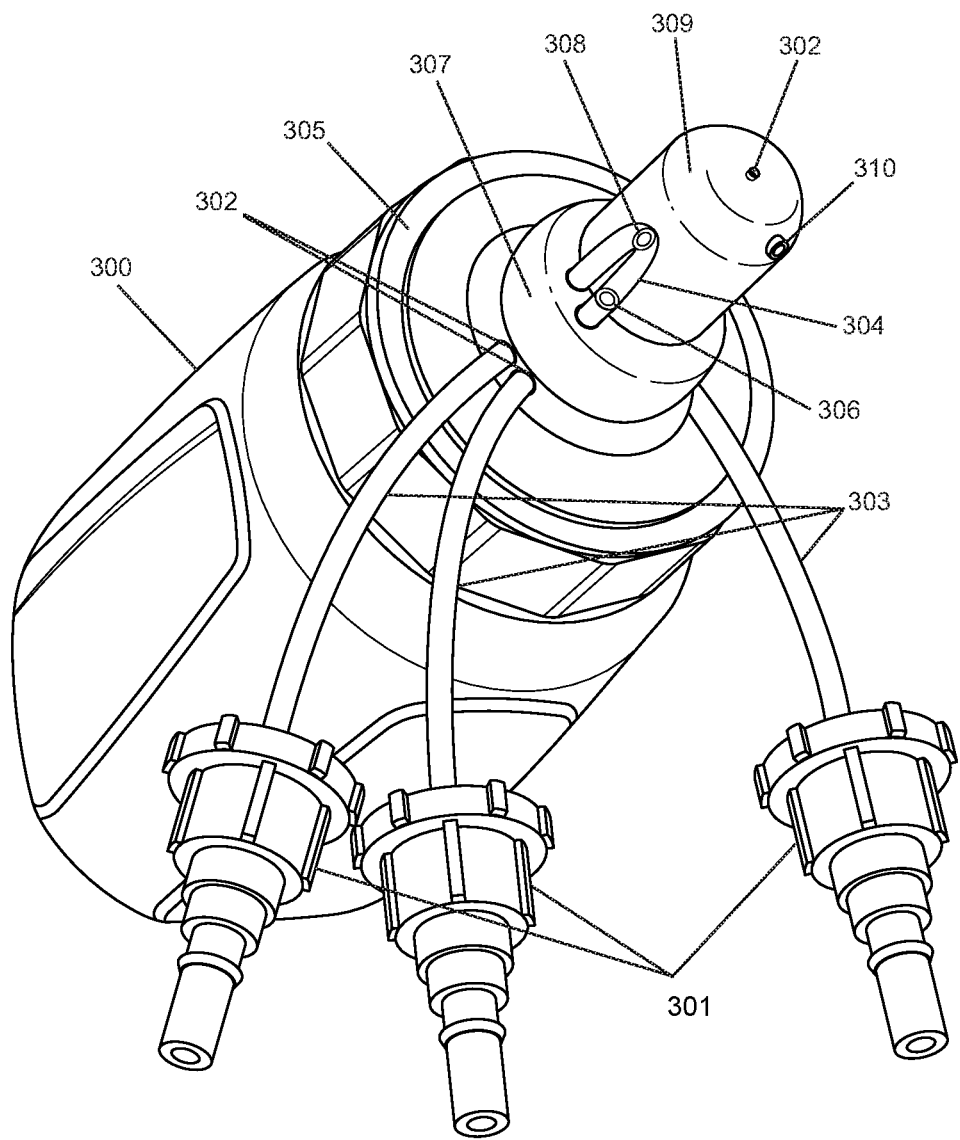
FIG. 3 is an isometric view of an example of an instrumented bottle nipple, attached to a bottle according to one embodiment of the present invention.

FIG. 3 illustrates an embodiment of an instrumented OMK nipple. FIG. 3 shows an assembly of a first embodiment of an OMK monitoring system, which is adapted for use with a bottle nipple 309. The Suction pressure is monitored with Mikro-tip pressure transducers 310 and the Expression pressures are monitored with Mikro-tip pressure transducers 306 and 308 (Model SPR-524, Millar Instr., Houston Tex.). The elements 310, 308, and 306 in FIG. 3 show the approximate placements of the pressure transducer plates (the transducer plate is the active, sensor part of the transducer that senses and responds to the applied pressure forces). For measuring the Suction component of sucking, the pressure transducer 310 is inserted through a polyethylene tubing (PE200, ID, Clay Adams, Becton Dickinson & Co, Parsippany, N.J.) flush to the tip of the nipple, without protruding into the infant's mouth. The nipple end of this PE 200 tubing is flared gently so as to anchor to the nipple. For measuring the Expression component, transducer 306 is positioned closer to nipple base 307. Transducer 308 is positioned near nipple tip 309.

Note that the examples shown in FIG. 3 illustrate another preferred feature of the improved OMK monitoring systems and devices, which is that the miniature pressure transducers measure pressure forces directly (i.e., the location where the actual forces are applied to), unlike standard ones that are remotely connected at a distance through air- or liquid-filled tubing, which have a risk of dampening amplitude of responses and delaying of event timing.

In FIG. 3, the Expression component is monitored using one or more micro-sized (one the order of 1 mm) pressure transducers 308 and 306. The transducer has an active, sensing head (the "transducer plate") that comprises a pressure-sensitive plate or membrane. Each transducer is inserted into a short (2.5 cm) piece of soft, transparent catheter tubing (Silastic, 1.3 mm ID, Dow Corning Corp, Midland, Mich.), which physically isolates the transducer from the infant's mouth. The short segment of soft, transparent catheter tubing is connected, in turn, to a longer section of stiff polyethylene tubing (PE 200). The short Silastic portion 304 is exteriorized along the outer surface of the nipple, in the relatively straight, mid-section/neck of the nipple. The Silastic tubing is transparent, which allows the pressure sensor to be visually inspected. The transducer plate can be positioned at any distance along the 'neck' of the nipple. To ensure the proper monitoring and recording of the Expression traces (pressure pulses/spikes), the pressure transducer plate is preferably positioned upward, where it can be pressed against the hard palate by the tongue pushing on the opposite, lower surface of the nipple. This optimizes the recording of the positive pressure generated by the tongue squeezing or stripping on the nipple against the hard palate, and standardizes the position of the tubing from one infant to another.

Figure 6A:
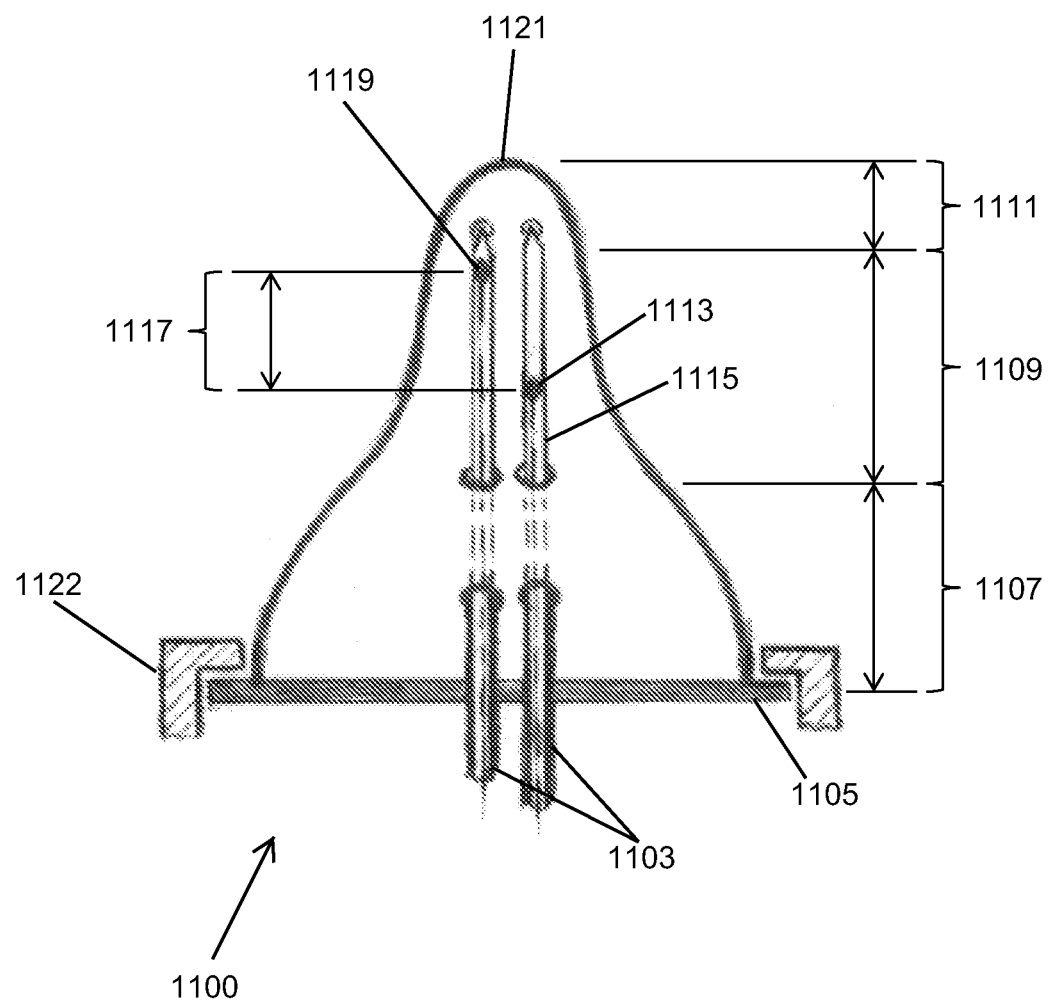
FIGS. 6A and 6B illustrate embodiments of an instrumented nipple.
Figure 6B:
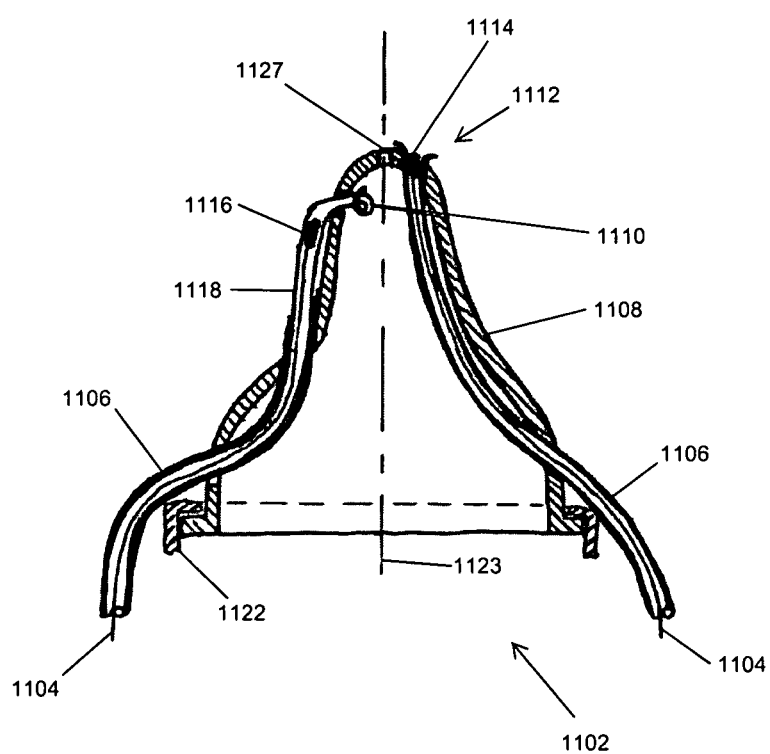

In FIG. 3, the Silastic piece 304 is connected to the PE tubing 303 by overlapping the tubings (FIG. 6B). The PE tubing enters the bottle at the base of the nipple 302. The transducer 306 and 308 and its wiring is inserted into PE tubing 303 through Silastic piece 304 until the pressure plate of 306 or 308 is at a desired distance from the tip of the nipple. The wiring of the transducer inside the PE tubing 303 is protected from damage. The overlap between Silastic 304 and PE tubing 303 is placed exactly at the site where the PE tubing 303 exit the base of the nipple. It is the elasticity of the nipple at the exit site that ensures the two tubings will not disconnect. The use of the soft Silastic 304 has three roles: 1) to prevent direct contact of milk with the pressure sensor, 2) to physically isolate the transducer from the infant's mouth, and 3) to prevent the possibility of any small parts detaching from the pressure sensor, and being ingested or inhaled by the infant during feeding. Tightening locks 301 at the distal (far) end of the each polyethylene tubing segment can be used to secure the positioning of the pressure transducers within the tubing.

As previously discussed, the Expression component of oral feeding generally comprises a combination of two different tongue actions (modes): 1) compression-only, where the tongue applies force perpendicular to the nipple's surface, without any lateral motion (i.e., no stripping), and 2) stripping, where the tongue moves (slides) laterally along the length of the nipple while also compressing the nipple. To determine if the mode of Expression consists primarily of "compression-only" or "compression plus stripping", two (or more) separate pressure transducers are mounted in the nipple's neck region. The two (or more) transducers are spaced apart (staggered) along the length of the nipple. When spaced sufficiently far apart, the staggered pair of transducers provides the ability to monitor and detect a unique "wave" signature that is characteristic of the stripping action. During "compression-only", the wave signature comprises a single pressure spike/pulse occurring at the same time at both transducers, which is generated when a tongue compresses all at once against the nipple. During "compression plus stripping" the wave signature comprises a pair of closely-spaced, sequential pressure spikes/pulses, which is generated when a tongue strips the nipple (typically, from nipple base to tip).

The embodiment shown in FIG. 3 comprises a pair of pressure transducers, each individually sheathed inside of their own Silastic catheter tubing segments, that are mounted alongside each other (side-by-side), and are oriented parallel to the nipple's long axis. One transducer plate is placed closer to the tip of the nipple ("nipple tip"). The other is spaced-apart approximately 1 cm farther away along the long axis of the nipple, and closer to the base of the nipple ("nipple base"). In the case of "compression only", the nipple is compressed by a non-translating tongue; and simultaneous (or, near simultaneous) pressure changes (spikes/pulses) are recorded from both of the spaced-apart transducers at the same time. In contrast, if the nipple is stripped by a moving tongue (e.g., sliding from nipple base to nipple tip), then a unique "wave" signature is generated by the pair of spaced-apart pressure transducers; with the wave signature comprising a pair of pressure spikes closely-spaced sequentially in time (depending on the tongue's striping velocity). A faster-moving tongue during striping would result in a shorter time interval being measured between the pair of pressure spikes from the spaced-apart transducers. Conversely, a slower-moving tongue during striping would cause a longer time interval to be measured between the pair of pressure spikes.

The embodiment shown in FIG. 3 can be successfully adapted to a pacifier or finger glove or nipple guard, for monitoring of oral motor kinetics during nonnutritive sucking (NNS).

A pacifier having an instrumented OMK nipple as described, may be used to monitor Sucking and Expression behavior during a nonnutritive sucking episode.

In general, an instrumented OMK nipple can be adapted/coupled to a variety of liquid sources, including: a regular (standard) bottle for routine feeding; a milk reservoir connected to the nipple chamber via a third catheter; any other types of special feeding bottles. Alternatively a transducer attached to a breast or a nipple shield can be instrumented as an OMK nipple.

Figure 4:
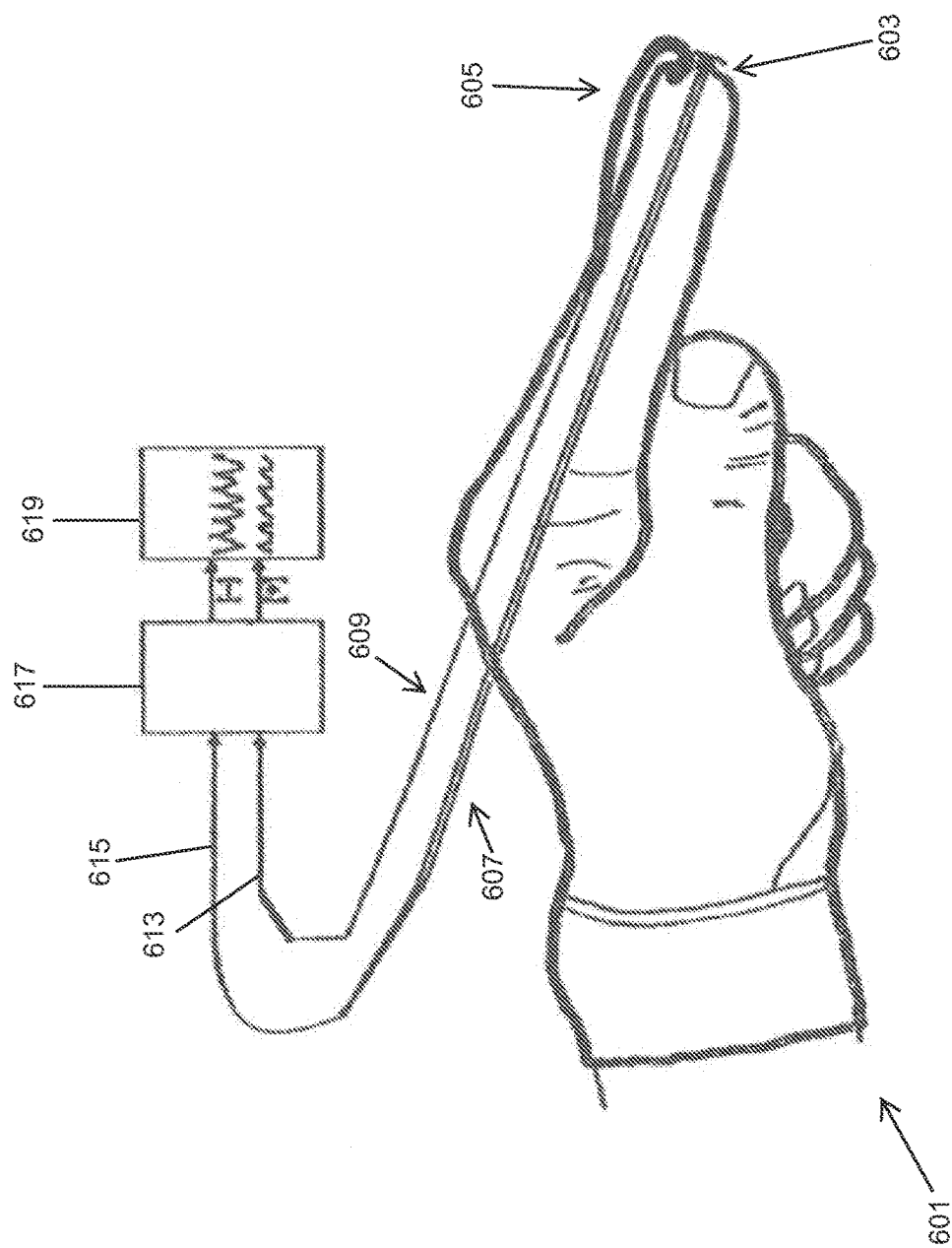
FIG. 4 is a schematic of an example of an instrumented disposable glove.

FIG. 4 shows another embodiment, where the pressure transducer configuration shown in FIG. 3 have been adapted onto a disposable glove 601, for assisting a feeding therapist in his/her clinical evaluation of a patient. This nonnutritive sucking (NNS), 'finger pressure' device is a novel and unique quantitative assessment tool. Its use, in conjunction with the routine assessment of anatomical and functional development of an infant's oral structures, allows therapists to obtain a more accurate evaluation of their patients' sucking skills. It can also be used as a teaching tool inasmuch as a subject's assessment can be compared between observers/students and reviewed.

In general, Suction and Expression pressure transducer signals (− and +, respectively) generated by an instrumented OMK system with transducer 603 and 605 sheathed within Silastic tubing located external to the glove 601. The Suction pressure signal 615 and the Expression pressure signal 613 from signal transducers 603 and inside 605 are carried through 607 and 609 to the signal processor 617 and recorded at 619; a system similar to that described in FIG. 1. An instrumented nipple can be combined with other monitoring systems that measure other physiological parameters, e.g., swallowing and respiration.

Figure 5:
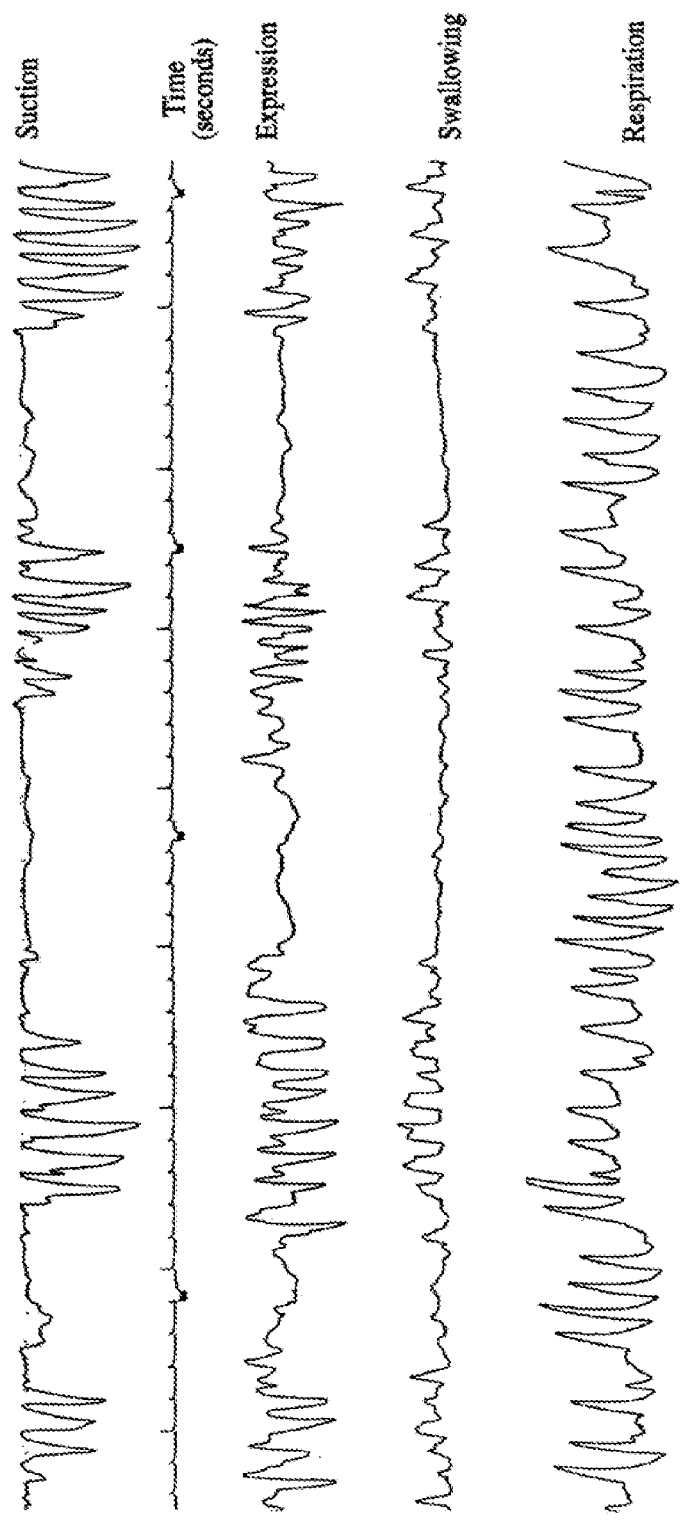
FIG. 5 is a sample tracing showing the simultaneous pressure traces of Suction, Expression, swallowing, and respiration.

A sample tracing illustrating this particular combination of signals, taken using an embodiment of an OMK system that is configured to allow for the simultaneous recordings of pressure signals indicative of Suction, Expression, swallowing, and respiration is illustrated in FIG. 5.

FIGS. 6A and 6B show schematic illustrations of an OMK instrumental nipple. The embodiment of FIG. 6A comprises a pair of pressure transducers 1117 on the nipple 1100. Each transducer individually sheathed inside of their own Silastic catheter tubing segments 1115, that are mounted parallel to each other (side-by-side), and are oriented parallel to the nipple's long axis as shown in 1123 of FIG. 6B. Three general regions of a bottle nipple are identified: the Tip-Section 1111, Mid-Section (Neck) 1109, and Base-Section 1107. The embodiment of FIG. 6B comprises a nipple 1102 having a crown ring 1122 that secures nipple 1102. For the transducer 1116, the wire 1104 is housed partly within PE tube 1106 securely connected to Silastic tube 1118. A knot at the end 1110 serves to anchor the Silastic tube. For the transducer 1112, the wire 1104 is housed within PE tube 1106 which shows a flared end 1112 flush to the nipple tip. The tube 1106 may be positioned next to the nipple sidewall 1108.

Figure 7:
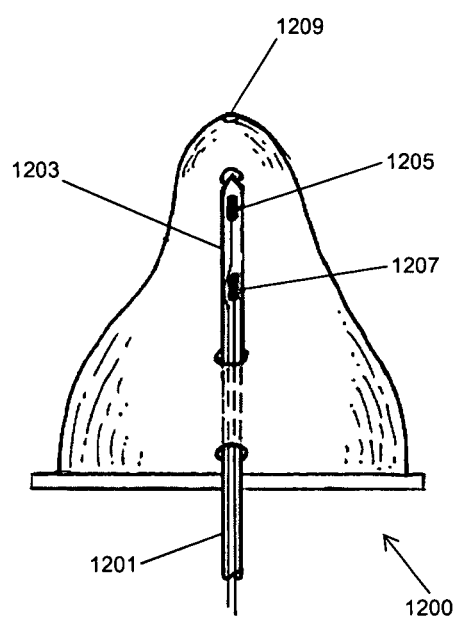
FIG. 7 illustrates an embodiment of an instrumented nipple.

FIG. 7 shows another embodiment of an instrumented nipple 1200 for an OMK system, comprising a pair of micro-pressure transducers 1205 and 1207 disposed together inside of the same catheter tubing segment consisting of a Silastic tubing 1203 connected to PE tubing 1201. The two transducer plates are spaced-apart from each other in the mid-section of the nipple (approximately 1 cm), front-to-back. This configuration (axially spaced-apart) allows the OMK monitoring system to distinguish between "compression-only" and "compression plus stripping" (wave) tongue motion during Expression. Pressure monitoring catheters with multiple high-fidelity pressure sensors, such as those from Millar Instruments, Houston Tex. can also be used. The nipple opening 1209 is located at the distal most portion of the nipple tip region with the transducer tip 1205 separated from the transducer base 1207.

Other Types of Pressure Sensors

The phrases: "pressure sensor", "pressure transducer", and "sensor/transducer plate" are used interchangeably herein. A micro pressure transducer plate would be an example of an active pressure-sensing element.

Any, or all, of the following types of pressure sensing/sensor methods, effects, materials, and/or active sensing elements can be used in any embodiment of the present invention (e.g., an instrumented OMK nipple) including, but not limited to: capacitive, resistive, piezoelectric, polyvinylidene fluoride (PVDF), microelectromechanical systems (MEMS) structures, and optical-type pressure sensing elements and methods.

Any pressure sensors/transducers, which use optical pressure sensing elements can comprise: a Fabry-Perot cavity pressure sensing element, a Mach-Zender interferometer pressure sensing element, and/or a Bragg grating pressure sensing element.

Alternatively, pressure sensors/transducers used in any embodiment of the present invention can comprise a 1-dimensional (linear) configuration, or a two-dimensional (planar) array (i.e., matrix) of pressure sensing elements. The pressure strips or pads can output a 1-D or 2-D map or profile of a (time-dependent, dynamic) pressure distribution along a line (straight or curved) or within an area (which can be flat or curved), respectively. An array of pressure sensing elements can be called by a variety of names, including: a pressure sensitive pad ("pressure pad"), a tactile sensor/sensing array, an artificial "electronic skin", a pressure mapping system, and a flexible pressure sensor. A substrate for holding/supporting the array of pressure sensing elements can be a rigid, semi-rigid, flexible, stretchable, or conformable substrate, depending on the application. The individual, active pressure sensing elements that make up the array can comprise any of the alternative types of pressure sensors listed above, including: capacitive, resistive, piezoelectric, PVDF, MEMS, and optical-type elements.

One or more pressure sensitive pads ("pressure pad") can be attached/bonded to any part or surface of the nipple, using any compatible material, including: adhesive, glue, pressure-sensitive adhesive tape, heat-welded, fusion-bonded, ultrasonic bonding, cyanoacrylate, BPA-free silicone parylene conformal coating. Alternatively, the pressure pad(s) can be embedded within the sidewall of the nipple, for example, during injection and blow molding. Alternatively, the pressure pad(s) can be located on the inside (inner/interior) surface of the nipple's sidewall.

Figure 8A:
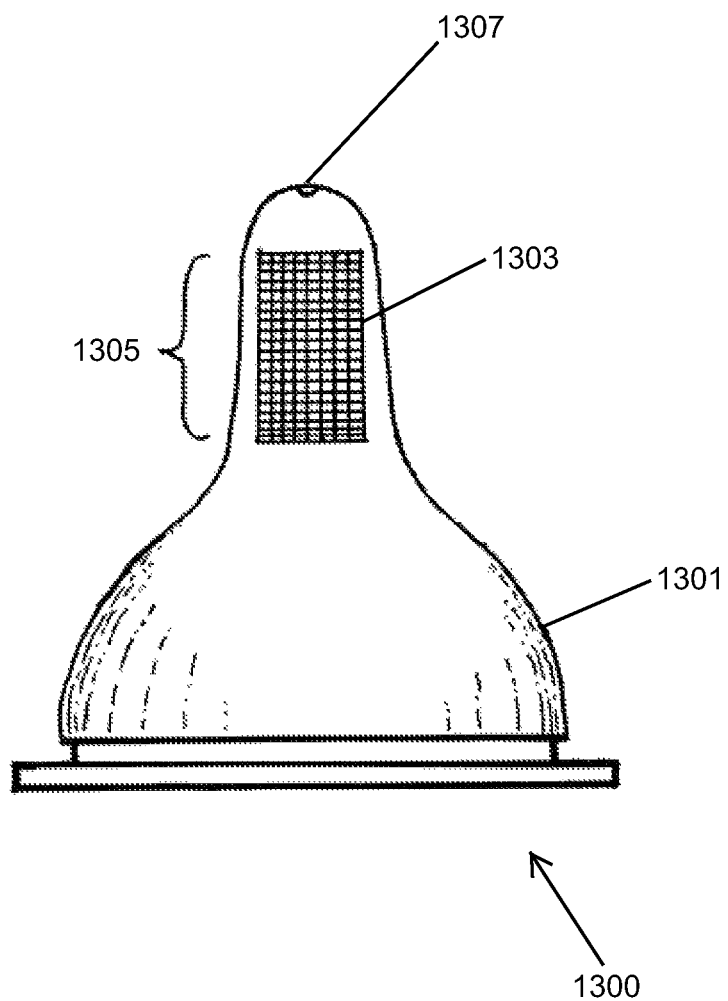
FIGS. 8A and 8B illustrate embodiments of an instrumented nipple.
Figure 8B:
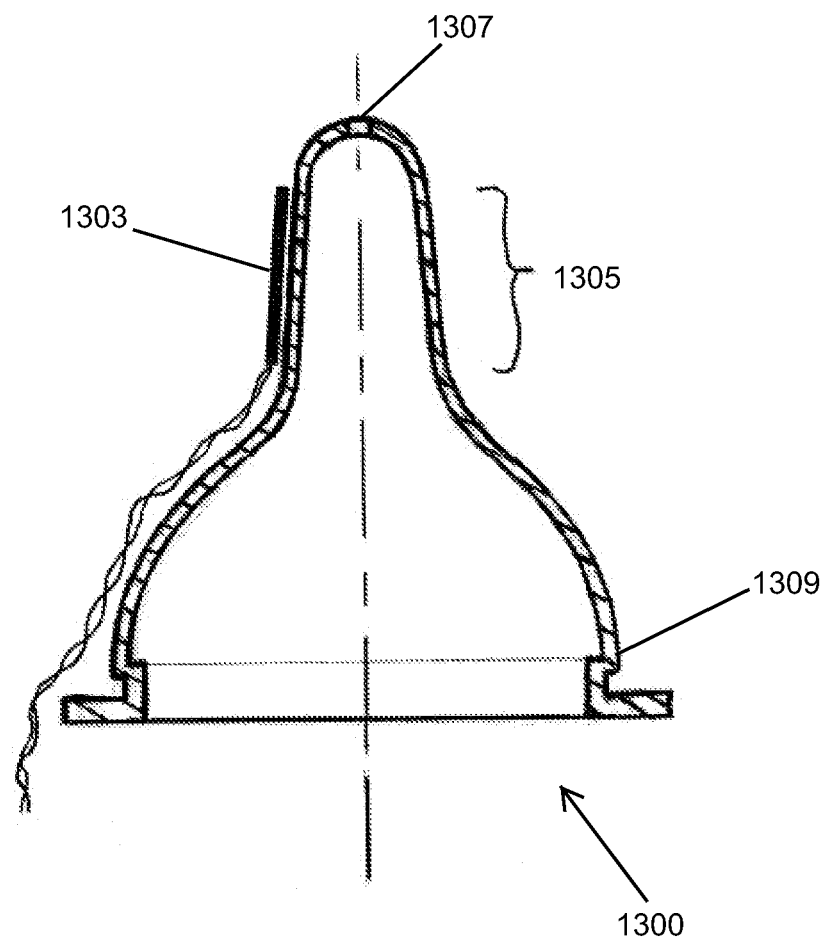

FIGS. 8A and 8B show another embodiment of an instrumented nipple for an OMK system 1300, comprising a 2-D pressure sensitive pad ("pressure pad" or "tactile sensing array") 1303 attached to the exterior surface of the mid-section (i.e., neck) 1305 of the nipple's sidewall 1301. The pressure pad in this embodiment comprises a 2-D array of pressure sensing elements (e.g., capacitive or resistive elements). FIG. 818/B shows a cross-section view of FIG. 8-A having a pressure pad 1303 attached to the exterior surface of the mid-section (i.e., neck) 1305 of the nipple's sidewall.

Another embodiment of an instrumented nipple for an OMK system, comprising a pressure pad that is embedded within, and surrounded by, the nipple's sidewall, at the nipple's neck (mid-section region). This embodiment is useful because the pressure pad is physically isolated from the environment of the infant's mouth; any pieces that separate or become loose are contained within the nipple wall. Also, the pressure pad's electrical leads (wires) are protected, and less prone to breakage, because they are located within the nipple.

Another embodiment of an instrumented nipple for an OMK system, comprising a 2-D pressure pad attached to the interior/inner surface of the mid-section (i.e., neck) of the nipple's sidewall. This embodiment is useful because the pressure pad is physically isolated from the environment of the infant's mouth; any pieces that separate or become loose are contained within the nipple cavity. Also, the pressure pad's electrical leads (wires) are protected, and less prone to breakage, because they are located inside the nipple.

Figure 11:
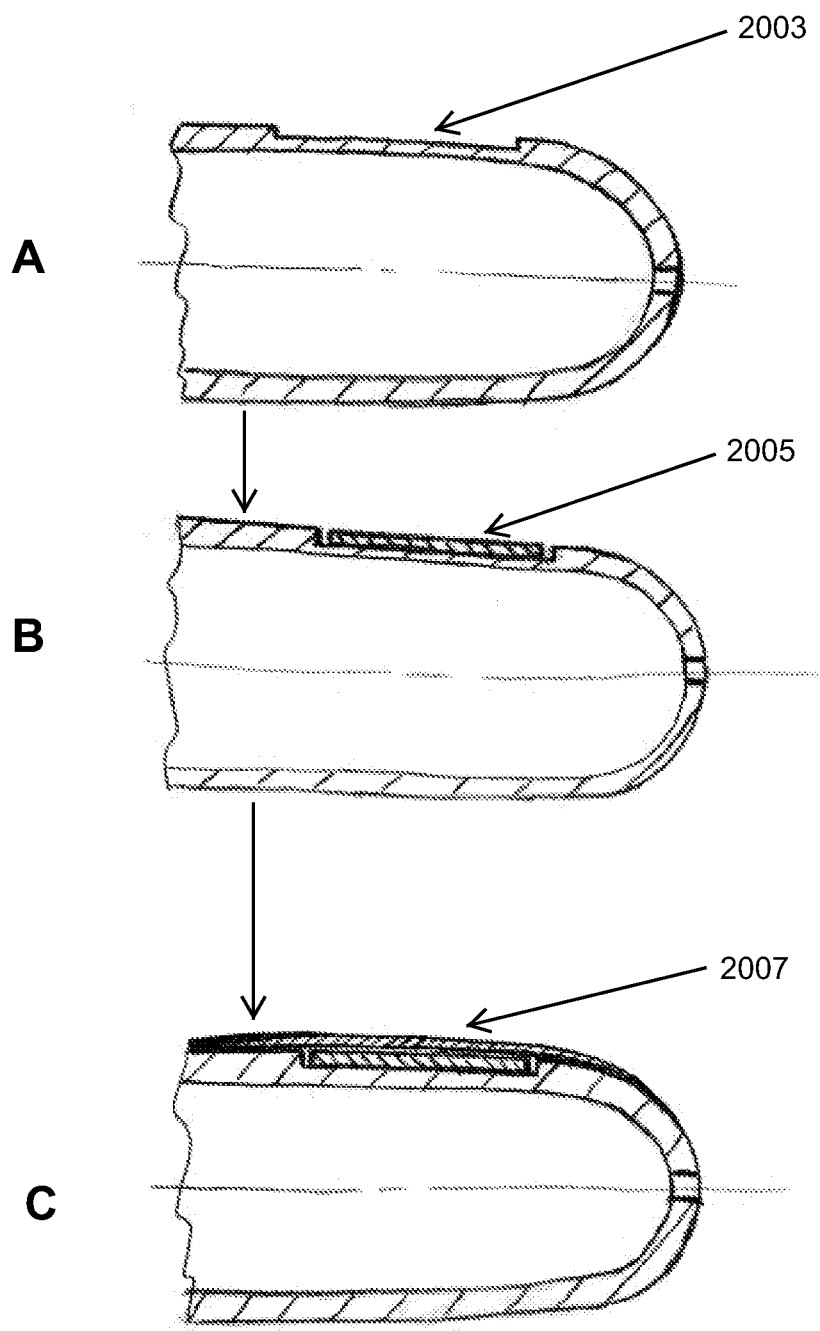
FIG. 11 illustrates multiple methods of making an instrumented nipple.

In general, a 1-D pressure array can be positioned at a variety of different locations, including, but not limited to: a) on the exterior surface of the nipple (as illustrated in the example of FIG. 11), or, alternatively, b) embedded within the sidewall of the nipple itself, or c) positioned inside of the interior wall of the nipple (e.g., glued to the inner surface of the nipple wall). Alternatively, the 1-D array can be held by a tube having the same diameter as the array, with the array's wires inside the tube. In some embodiments, such a tube can be held by a rigid grid that is fit at the base of the nipple and held in place by the nipple crown (i.e., crown ring).

Figure 9:
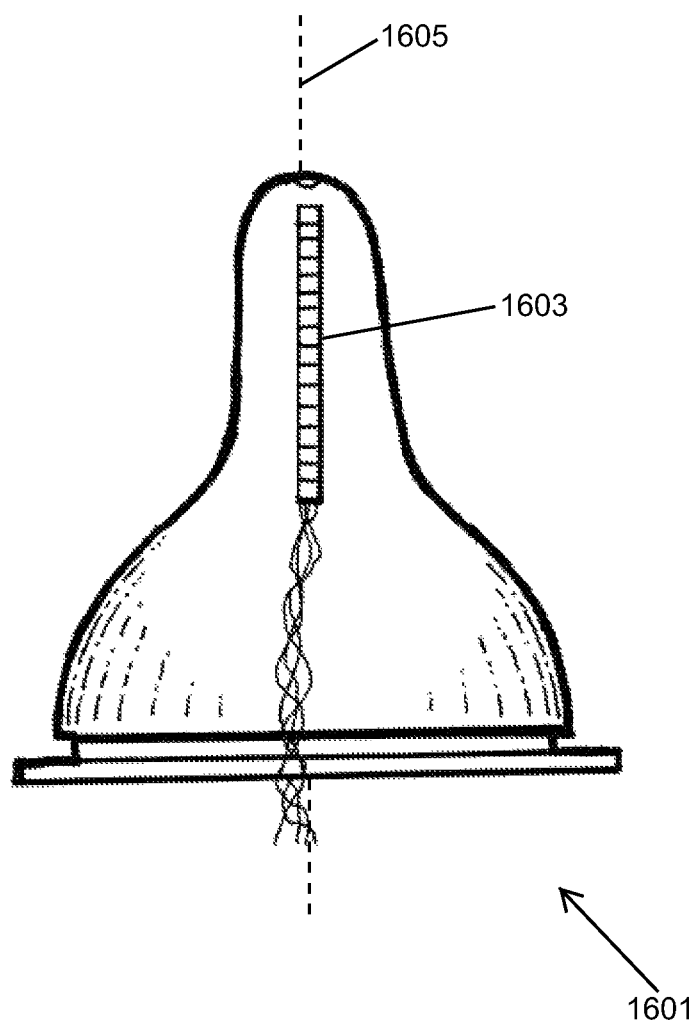
FIG. 9 illustrates an embodiment of an instrumented nipple.

FIG. 9 shows another embodiment of an instrumented nipple for an OMK system 1601; comprising a 1-D, linear array of pressure sensing elements 1603 (i.e., a linear strip of pressure sensing elements). In this embodiment, the orientation of the 1-D, linear pressure-sensing array is aligned parallel to the nipple's centerline 1605.

Another embodiment is an instrumented pacifier or fingerglove or nipple shield for an OMK system, comprises a 2-D tactile sensing array (i.e., pressure pad), for monitoring sucking and Expression in a non-nutritive setting. Alternatively (not shown), a 1-D linear array of pressure sensing elements (i.e., a linear pressure strip), can be attached to the pacifier or finger gloves or nipple shield.

In other embodiments, a 1-D linear array of pressure sensing elements (i.e., a linear pressure strip), can be attached to a finger of the glove (in addition to, or in place of, a 2-D pressure pad). Alternatively, a 1-D linear pressure strip can be placed on one finger of the glove, and a 2-D pressure pad can be placed on a different finger of the same glove (e.g., on an adjacent finger). Alternatively, a 1-D linear pressure strip can be attached (i.e. taped) directly to a person's finger underneath a glove.

Figure 10A:
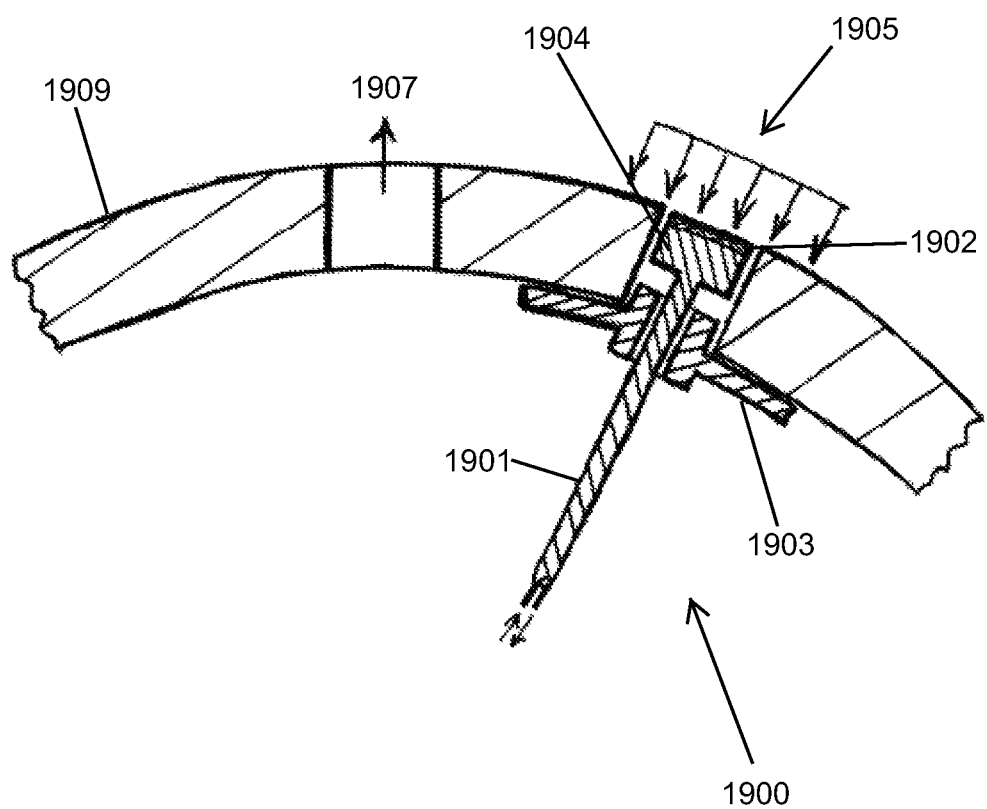
FIGS. 10A and 10B illustrate embodiments of an instrumented nipple.

FIG. 10A shows another embodiment of an instrumented nipple for an OMK system 1900, wherein the sensor for measuring the intra-oral pressure 1905 (i.e., inside of the infant's mouth) comprises a fiber optic pressure sensor 1901. The fiber optic sensor is located close to the nipple's orifice 1907, and the active head/sensing surface 1904 is mounted flush with the nipple's outer surface, through an access hole 1902 in the nipple's sidewall 1909. A retaining clip 1903 can be used to hold the sensor in place.

Figure 10B:
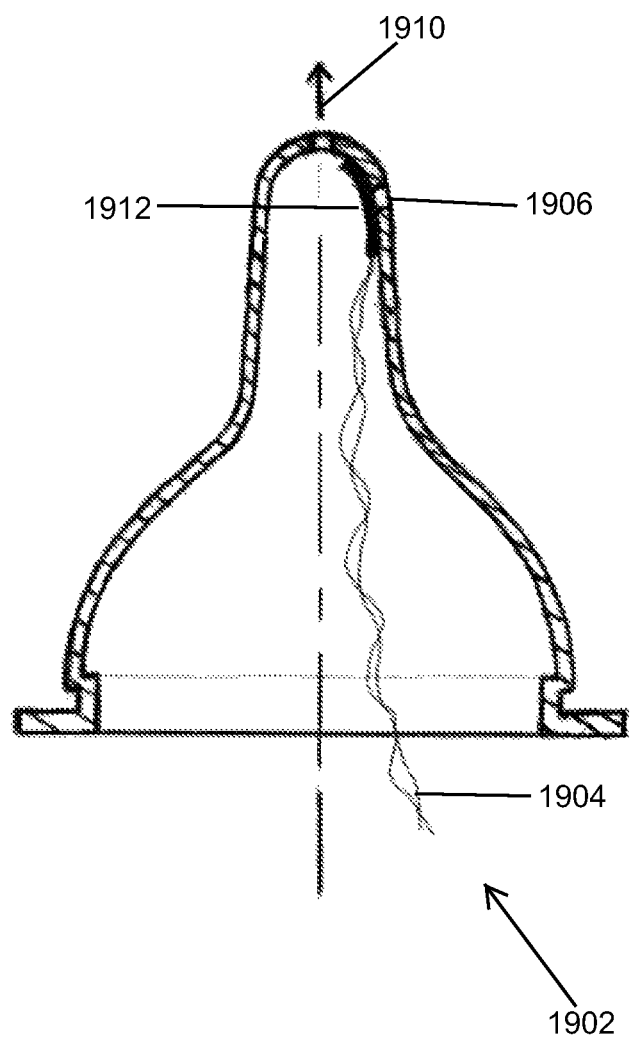

FIG. 10B shows another embodiment of an instrumented nipple for an OMK system 1902, wherein the sensor 1912 for measuring the intra-oral pressure (i.e., inside of the infant's mouth) comprises a 2-D pressure sensitive array (pressure pad) that is attached (e.g., adhesively bonded) to the inside of the nipple's sidewall, covering a $2^{nd}$ hole/opening 1906 in the nipple's sidewall near the tip. Near the opening 1910, the $2^{nd}$ hole 1906 provides access through which the pressure pad can sense (measure) the pressure outside of the nipple (i.e., the intra-oral pressure). The backside of the pressure pad may have a waterproof backing or coating (e.g., silicone coated, epoxy-coated, Gore-Tex membrane), to prevent milk from leaking out through the $2^{nd}$ hole. The $2^{nd}$ hole should be large enough in diameter to provide sufficient access to the pressure pad, through the hole, by the negative pressure inside the mouth generated when sucking. Leads 1904 may be present to connect transducer 1912 to a recording device (not shown).

FIGS. 11A, 11B and 11C show an example of a 3-step process for making an instrumented nipple for an OMK system. Panel A illustrates a recessed pocket 2003 is formed in the sidewall of the nipple's neck region. The depth of the pocket can be, for example, ½ of the thickness of the sidewall. The recessed pocket 2003 can be formed during injection molding of the nipple (e.g., a silicone nipple). The size of the pocket is slightly larger than the size of the pressure pad 2005. Alternatively, the pocket can be ablated away by a rastered laser. Panel B illustrates a pressure pad 2005 is placed into the recessed pocket 2003. Optionally, the pad can be glued to the nipple. Panel C illustrates, a protective coating is applied over the pressure pad 2007, to form a hermetic seal, and to physically isolate the pad from the environment of the infant's mouth. The coating can extend beyond the edges of the pocket, with the edges of the coating thinned/feathered down. The coating is preferably made of a biocompatible material (e.g., silicone).

Fluid Flow Rate Sensor

A coarse measurement can be made of the average volume of milk swallowed by an infant per suck (i.e., a "bolus") by measuring or weighing the total volume of milk removed from a bottle during a feeding session and dividing that by the total number of sucks counted by an observer. However, this doesn't provide any information on the instantaneous flow rate during a suck, or the bolus of milk for a single suck.

In some embodiments of the present invention, the OMK monitoring system comprises a flow sensor means for measuring a volumetric (e.g., ml/s) and/or mass flow rate (e.g., g/s) of a fluid (e.g., milk) flowing out of a nipple during feeding. Preferably, the flow sensor means can measure, as a function of time, the instantaneous velocity or volumetric (or mass) flow rate of fluid flowing out of a nipple. An OMK monitoring system can comprise a flow sensor as the only instrumentation; or, alternatively, the system can additionally comprise other types of sensors (e.g., pressure sensor(s), optical sensor, temperature sensor, etc.).

The flow sensor means for measuring an instantaneous fluid flow rate ("flow sensor") can utilize or comprise any of a wide variety of methods, devices, and structures that measure/respond to physical properties of a moving fluid (e.g., velocity, and, hence, volumetric or mass flow rate; pressure; density; etc.), including, but not limited to: pressure differential or pressure drop across a flow discontinuity or restriction (e.g., Venturi, calibrated orifice plate), ultrasonic techniques, thermal properties technique (e.g., Resistance Temperature Detectors (RTD) thermistor, hot-wire technique, thermal flow sensor), MEMS micro flow sensor, electrochemical techniques (electrolytes, electrical admittance, "Lab-on-a-Chip"), MEMS Coriolis-effect flowmeter (resonant tube), semiconductor field effect, Particle Image Velocimetry (PIV), and flow-based laser or optical techniques, as described below.

The volume of liquid (bolus, in ml) passing through the flow sensor, for a single suck, can be calculated by integrating the instantaneous measured flow rate (ml/s) over time, for the duration of the single suck. A typical bolus volume (per suck) is in the range of 0.1-0.4 ml. A typical volumetric flow rate during feeding is in the range of 0-6 ml/min.

A. Flow Rate Sensor Integrated with/within Nipple

A first class of flow rate sensors comprises one or more sensing elements that are integrated with or within the nipple itself (bottle nipple, nipple shield). With the use of miniature/micro-sized transducers (e.g., pressure transducers) and MEMS manufacturing techniques, it is possible to fabricate fluid flow sensors that are small enough to fit inside the rounded tip region of a nipple, or inserted into the nipple's exit hole. This is particularly useful, because the fluid flow properties (e.g., velocity, density, mass flow rate, volumetric flow rate) are preferably measured right at the point where the fluid leaves the nipple (i.e., the nipple exit hole).

Figure 12:
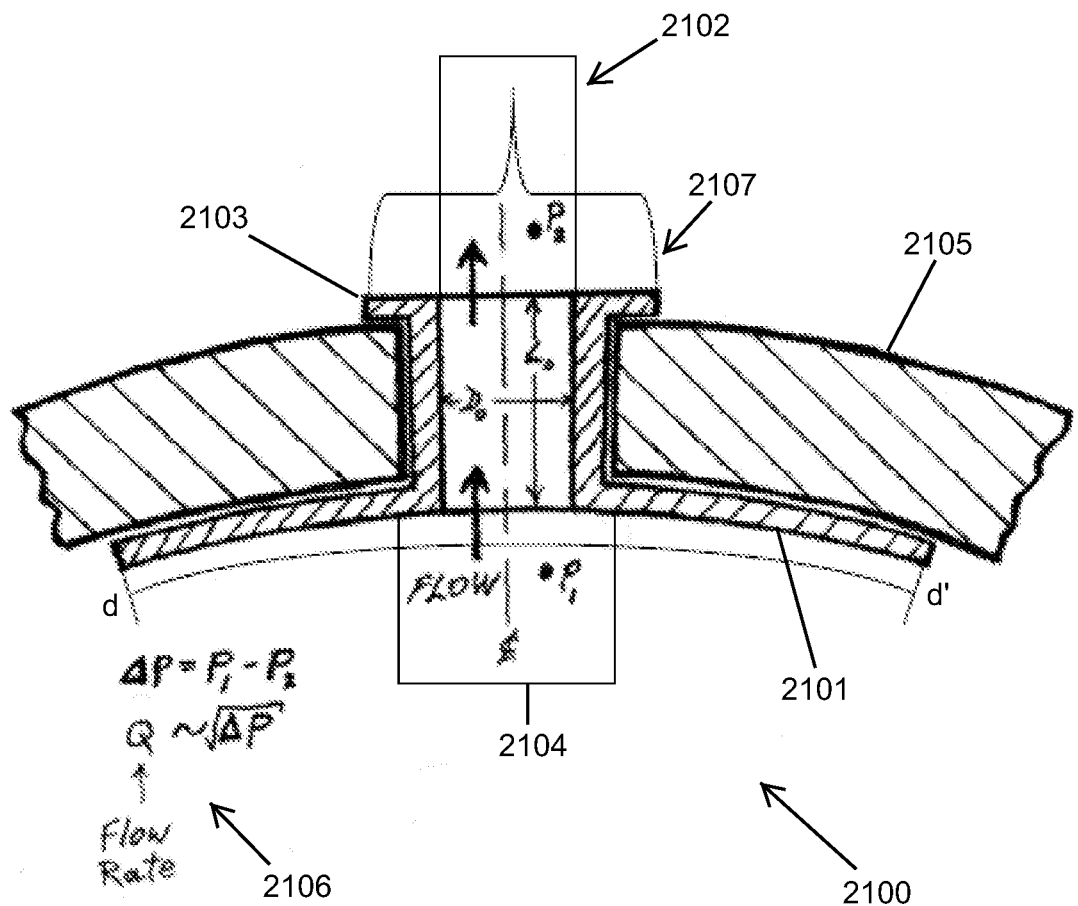
FIG. 12 illustrates an embodiment of an instrumented nipple.

FIG. 12 shows an embodiment of an instrumented nipple for an OMK system 2100, comprising a calibrated flow orifice 2102 having a diameter of $D_o$ and a length of $L_o$ is inserted into the standard flow/exit hole 2104 at the tip of the nipple. The calibrated flow orifice insert 2107 is formed out of a rigid material (e.g., polycarbonate plastic, aluminum, stainless steel) that will retain its shape during use. Unlike the standard hole in a silicone or latex nipple (which changes shape from a circle to an ellipse over time due to non-uniform stretching, and which may have small cracks from ageing or fatigue), the calibrated orifice insert comprises an orifice with a constant inner diameter, $D_0$, and a constant length, $L_0$; both of which have been measured with a high degree of accuracy. The cross-sectional shape of the calibrated flow orifice is typically circular; however it can have any shape (e.g., oval, hexagonal, octagonal), just so long as the shape stays constant over time and doesn't change or distort. The flow rate formula is shown at 2106.

The calibrated orifice insert 2107 in FIG. 12 has an integral inside/inner flange 2101 with a large diameter $(d-d^1)$, which prevents the orifice from being accidently dislodged from the nipple and being ingested or inhaled by the infant. The calibrated orifice also has an integral outer lip 2103, having a smaller diameter as compared to the inside flange, for retaining and securing the orifice to the nipple sidewall 2105 (which has a typical thickness of 1 mm used in a human infant baby bottle). The inside flange and the outer lip can be circumferentially axisymmetric (i.e., continuously circular). Alternatively, the inside flange and/or the outer lip can comprise a plurality of non-axisymmetric tabs or wings, e.g., 3-6 tabs (not illustrated). Preferably the calibrated flow orifice insert fits tightly inside the nipple's hole, and seals well to the nipple's sidewall 2105, in order to prevent any fluid from flowing in gaps and bypassing the main flow through the orifice open channel.

In general, the dimensions (length and diameter) of an orifice insert can be adjusted and optimized to produce a larger (or smaller) pressure drop, as needed, to better match the typical fluid flow rates generated by an infant during an oral feeding session.

Once the orifice has been calibrated, then the fluid flow rate is proportional to the square root of the pressure drop, $\Delta P$, where $\Delta P = P_1 - P_2$ 2106, between the pressures at the inlet and outlet of the orifice. The calibrated orifice is typically pre-calibrated at the manufacturer by accurately measuring the flow rate as a function of pressure drop across the orifice. This results in a linear, straight-line plot with minimal scatter of data points.

In the device of FIG. 12, the inlet pressure, $P_1$, can be measured by any type of micro-pressure transducer, fiber optic pressure transducer, etc., at a point inside of the nipple and close to the tip. The transducer(s) optionally can be attached to the orifice. The outlet pressure, $P_2$, is the same as the intra-oral pressure inside the infant's mouth, which can be measured by any type of micro-pressure transducer, fiber optic pressure transducer, etc. that has been inserted through the nipple's sidewall and into the intra-oral space to monitor the pressure inside of the infant's mouth, but without protruding into the baby's mouth (see, e.g., FIGS. 3).

Figure 13A:
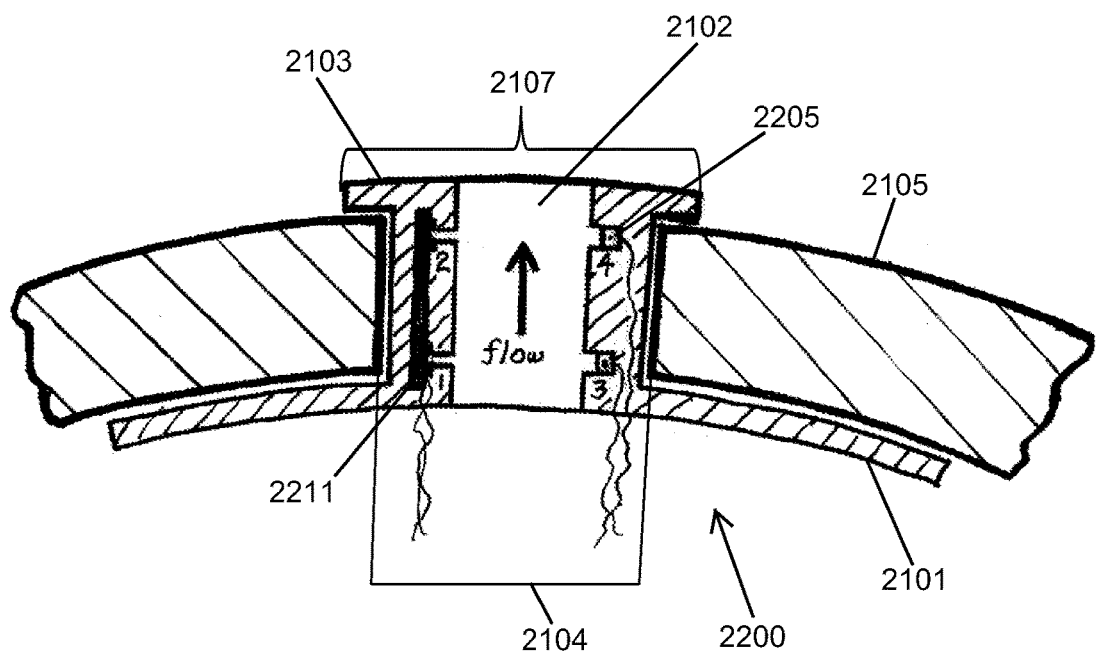
FIGS. 13A, 13B, 13C and 13D illustrate embodiments of an instrumented nipple.

FIG. 13A shows another embodiment of an instrumented nipple for an OMK system 2200, comprising a calibrated flow orifice 2102 inserted into the standard flow/exit hole at the tip of the nipple. FIG. 13A is similar to FIG. 12, except that the pressure drop is measured at two different points located inside of the orifice's channel.

Two different examples of means for measuring pressure are illustrated schematically in FIG. 13A. On the left hand side of the orifice, two MEMS-based pressure sensors 2211 (measuring $P_1$ and $P_2$) are disposed on a substrate, which, in turn, is embedded within the thick sidewall of the calibrated orifice 2102. Small ports (horizontal holes) 1 and 2 connect individually the two MEMS pressure sensors to the pressurized fluid flowing inside the orifice. The fluid flow rate is proportional to the square root of the pressure drop, $\Delta P_{1-2}$, where $\Delta P_{1-2}=P_1-P_2$.

On the right hand side of the orifice in FIG. 13A, two MEMS-based fiber optic pressure sensors 2205 (measuring pressures $P_3$ and $P_4$) are embedded in the thick sidewall 2105 of the calibrated orifice. Small ports 3 and 4 (horizontal holes) individually connect the two fiber optic pressure sensors 2205 to the pressurized fluid flowing inside the orifice, or, alternatively, the head of the fiber optic sensor can be mounted flush with the surface, which puts the sensor in direct contact with the fluid. The fluid flow rate is proportional to the square root of the pressure drop, $\Delta P_{3-4}=P_3-P_4$. The two different pressure drops should match each other closely.

The pair of laser fiber optic pressure sensors can be, for example, a model No. OPP-M25, manufactured by OpSens, Inc., in Quebec, Canada (www.opsens.com). This model has an outer diameter of the sensing head of 0.25 mm (250 microns), a pressure range of −50 to +300 mm Hg, a precision of +/−2 mm Hg, and a resolution of 0.5 mm Hg. OpSens also makes a larger fiber optic pressure sensor, OPP-M40, with a 0.4 mm (400 microns) OD of the sensing head. The smaller model, OPP-M25, is the smallest MEMS based optical pressure sensor available on the market today, and is used in a wide variety of medical applications, including: cardiovascular, intracranial, intrauterine, intraocular, intervertebral disc, urodynamic, and compartment pressure measurements. The optical sensor is immune to interference from radio frequency (RF) fields, magnetic resonance imaging (MRI) fields, and electromagnetic radiation from electro-surgery tools.

Figure 13B:
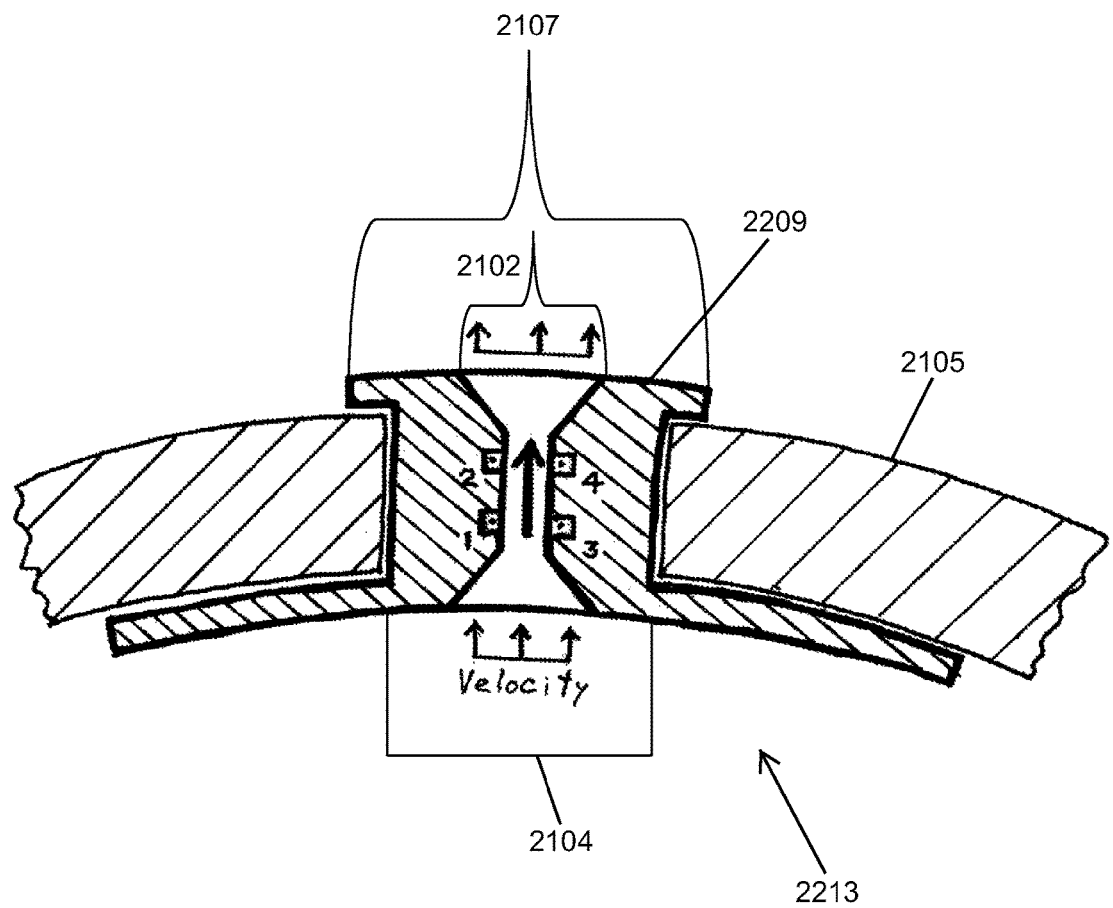

A principal difference between the embodiment shown in FIGS. 13A and 13B, and the embodiment of FIG. 12, is that all of the pressure sensors in FIGS. 13A and 13B are small enough that they can be embedded inside of the relatively-thick sidewalls of the orifice 2105, which makes for a more compact, and more hygienic and safer piece of instrumented equipment.

In contrast, the pressure transducers in FIG. 12 are mounted outside of the orifice.

FIG. 13B shows another embodiment of an instrumented nipple for an OMK system 2213, comprising a calibrated flow orifice 2102 inserted into the standard flow/exit hole 2104 at the tip of the nipple. FIG. 13B is identical to FIG. 13A, except that the orifice in FIG. 13B comprises a necked-down region that creates a much higher flow velocity in the straight test section (i.e., the gauge length/section). The smaller diameter of the necked-down region, coupled with the higher flow velocity, results in a much higher pressure drop, $\Delta P_{1-2}=P_1-P_2$ and $\Delta P_{3-4}=P_3-P_4$.

The dimensions (length and diameter) of the necked-down region in FIG. 13B, and the larger diameters of the inlet and outlet of the orifice insert can be adjusted and optimized to produce a larger (or smaller) pressure drop, as needed, to better match the typical fluid flow rates generated by an infant during an oral feeding session.

Figure 13C:
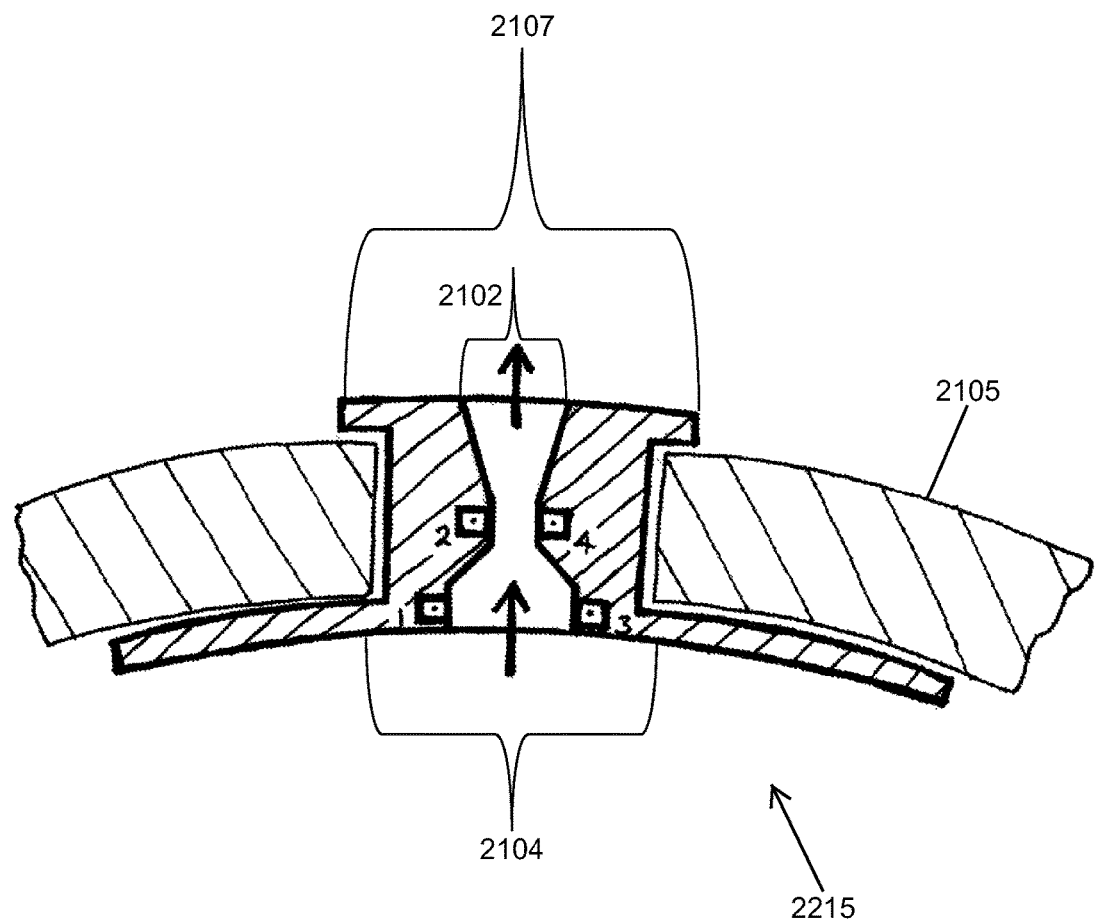

FIG. 13C shows another embodiment of an instrumented nipple for an OMK system 2215, comprising a calibrated flow orifice 2102 inserted into the standard flow/exit hole 2104 at the fluid delivery opening of the nipple. FIG. 13C is identical to FIG. 13B, except that the orifice in FIG. 13C comprises a Venturi-type necked-down region that creates a much higher flow velocity in the compressed region. With the Venturi-type geometry, the pressures are measured at different locations that in FIG. 13B. However, the pressure drop equations are the same, i.e., $\Delta P_{1-2}=P_1-P_2$ and $\Delta P_{3-4}=P_3-P_4$. In a Venturi-type flow rate sensor, the volumetric flow rate, Q, is proportional to the square root of the pressure drop $\Delta P_{1-2}$.

Figure 13D:
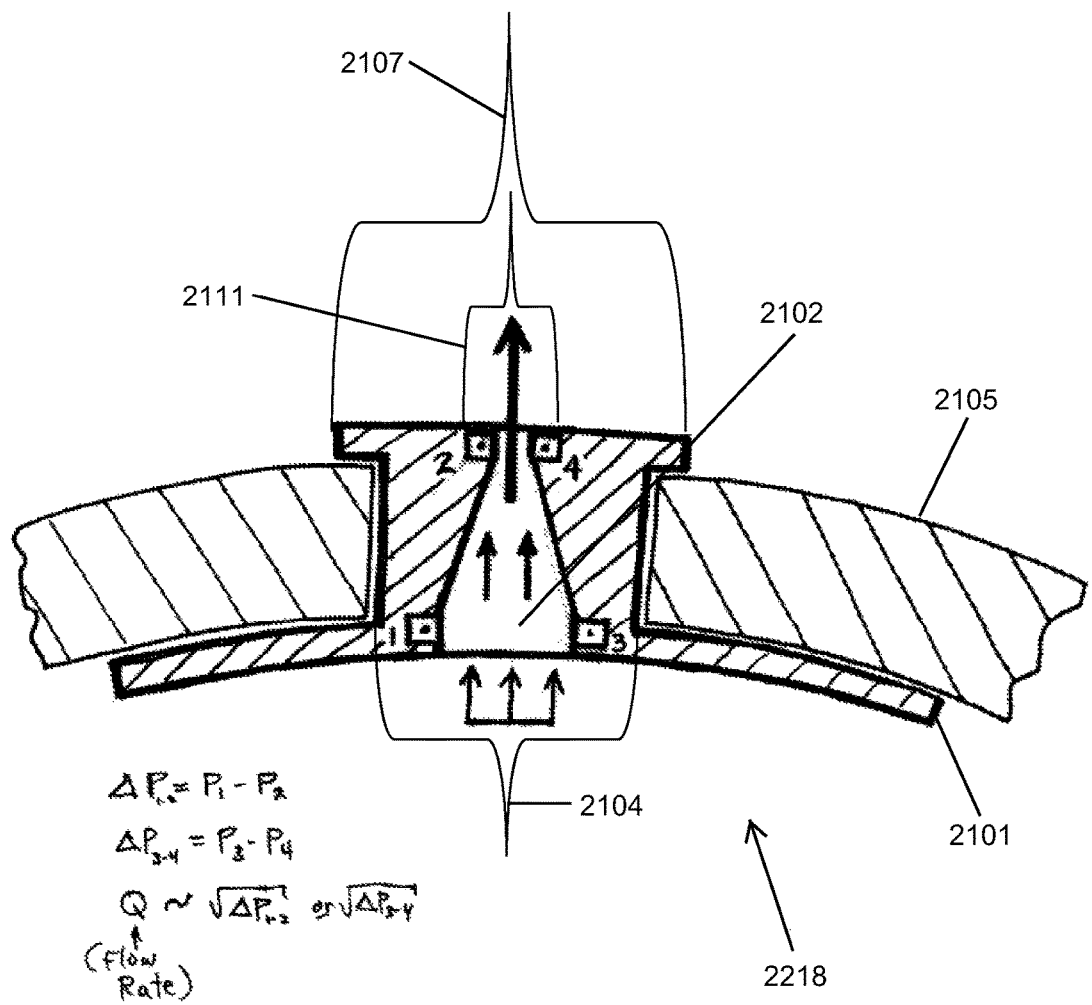

FIG. 13D shows another embodiment of an instrumented nipple for an OMK system 2218, comprising a calibrated flow orifice 2102 inserted into the standard flow/exit hole 2104 at the tip of the nipple. FIG. 13D is identical to FIG. 13C, except that the orifice 2102 in FIG. 13D comprises a compressed, funnel-shaped, flow channel that creates an even greater flow velocity at the exit of the compressed end of the orifice. The use of a compressed, funnel-shaped flow channel design for the calibrated flow orifice insert will generate higher pressure-drops across the orifice that result in accelerated flow (4×) 2111.

Figure 14:
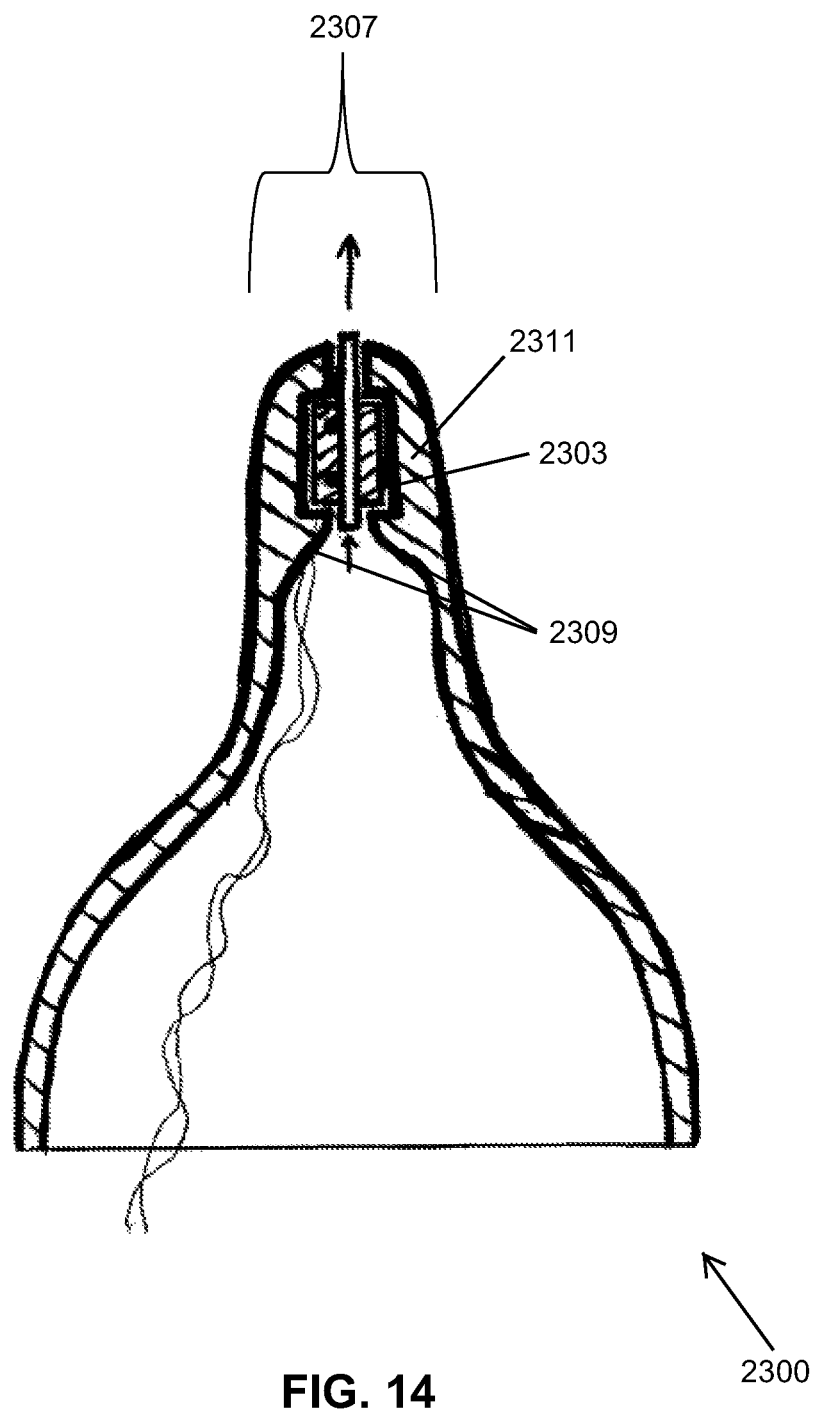
FIG. 14 illustrates an embodiment of an instrumented nipple.

FIG. 14 shows other embodiments of an instrumented nipple for an OMK system 2300, comprising a fluid flow rate sensor 2303 mounted inside of a nipple, placed close to the rounded tip 2307. The OMK nipple has been modified to provide a plurality of injection-molded features (e.g., indentations, protrusions, shoulders, bumps) to support and grip the flow sensor's housing (which can be cylindrical). The molded indentations in FIG. 14 can be continuous circumferentially; or, alternatively they can be discontinuous circumferentially.

In the embodiment shown in FIG. 14, the molded shoulder tabs/wings/grips 2309 are discontinuous in the circumferential direction. During installation of the flow sensor, this feature (discontinuous tabs/wings/grips) allows the nipple's neck to be temporarily stretched/pulled radially outwards. This opens up the molded grips radially, and permits the flow sensor to be inserted into the nipple and past the tabs/wings/grips, as far as possible towards the tip. Then, after the releasing the neck, the tabs/wings/grips contract radially inward and grab/hold onto the sensor. In an alternative embodiment the molded shoulder grips are absent.

Figure 1:
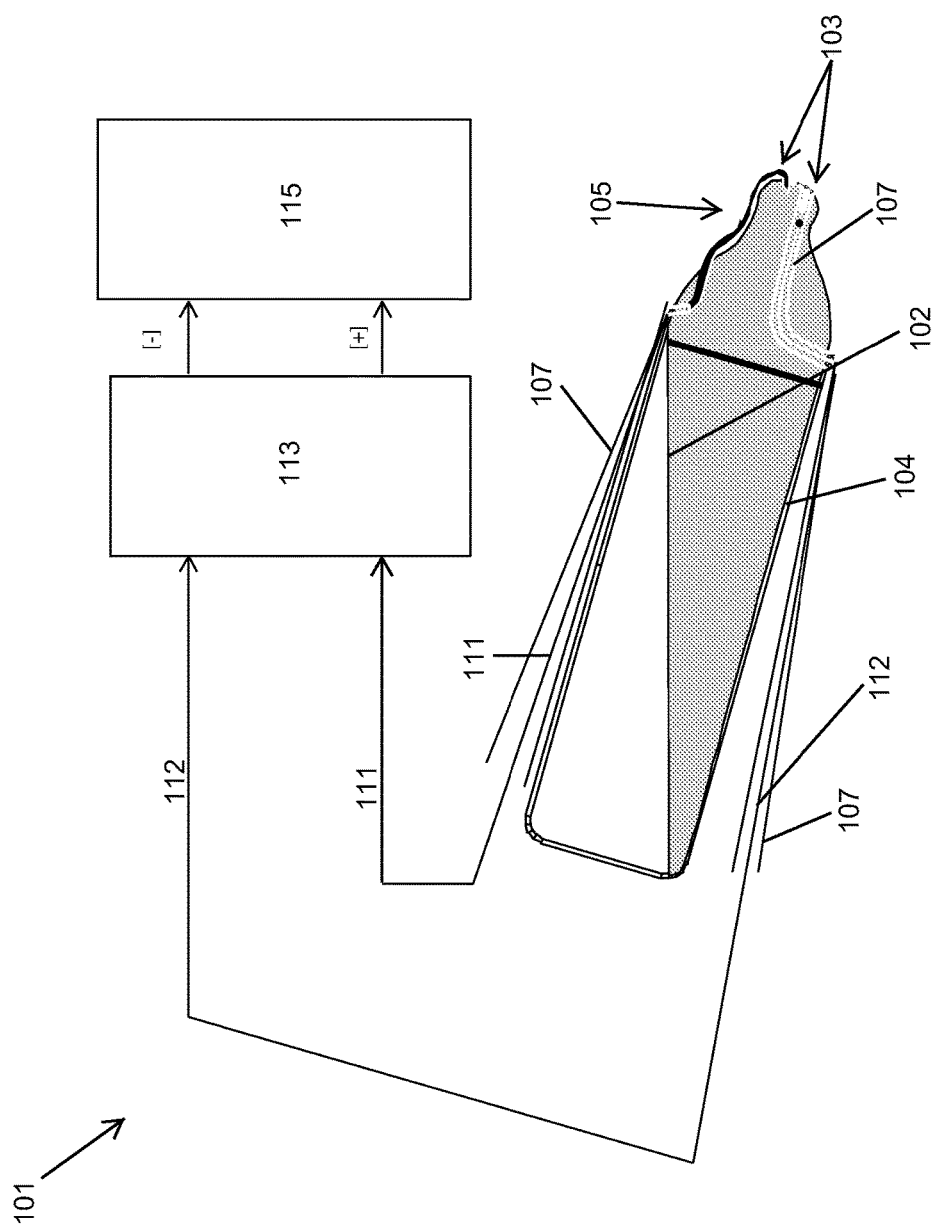
FIG. 1 is a schematic of an example of an instrumented nipple according to one embodiment of the present invention, adapted to a recording device, for the measurement of Suction and Expression pressures during bottle-feeding.
Figure 2:
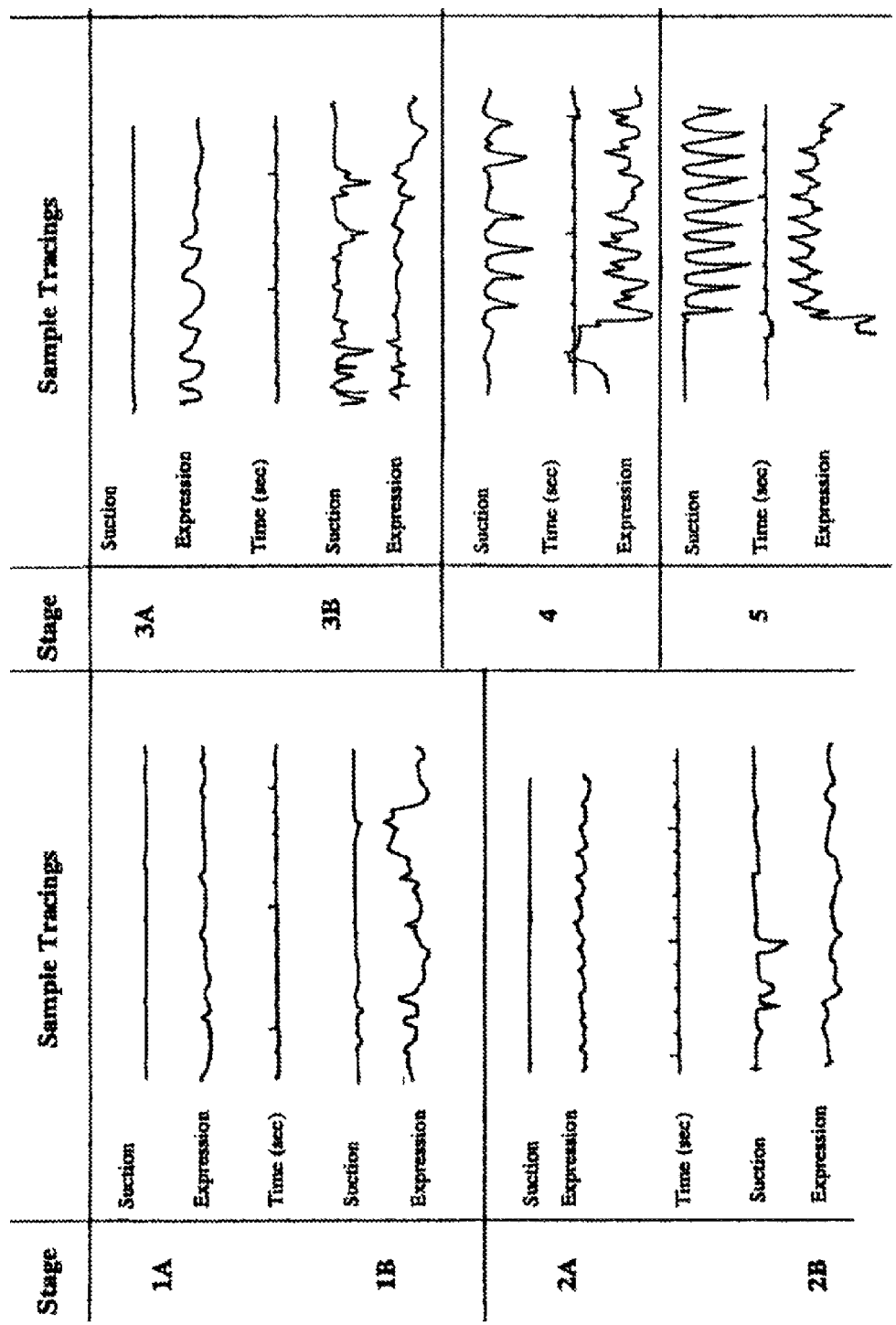
FIG. 2 shows the different stages of sucking, Suction and Expression, as infant matures monitored with an OMK system.

In some embodiments, the bottle nipple is modified to make it easier to use with miniature/micro pressure sensing catheters (e.g., Millar transducers, where the pressure sensing transducer plate(s) are mounted at the distal end of a small diameter (e.g., less than 1 mm dia.) catheter). The bottle nipple is modified so that the nipple has a section comprising thicker (i.e., thickened) sidewall located on the hard palate side (i.e., the side that would be against the infant's hard palate), and a normal-thickness sidewall on the side facing the infant's tongue. One or more channels or tunnels are disposed within the thickened sidewall section. The thickened sidewall makes the nipple slightly asymmetric (non-symmetric) with respect to the nipple's central axis. The tunnel also contains any parts of a pressure-sensing catheter that might come loose, and prevents those parts from being swallowed or inhaled by the infant. A disadvantage of inserting the pressure transducers within the tunnels is that the amplitude of the pressure signal will be reduced (dampened), as compared to the externalized transducers that are covered with the thin Silastic sheath (as shown in FIG. 1). They will be externalized at the base of the nipple, like it is currently done (see FIG. 1).

Figure 22A:
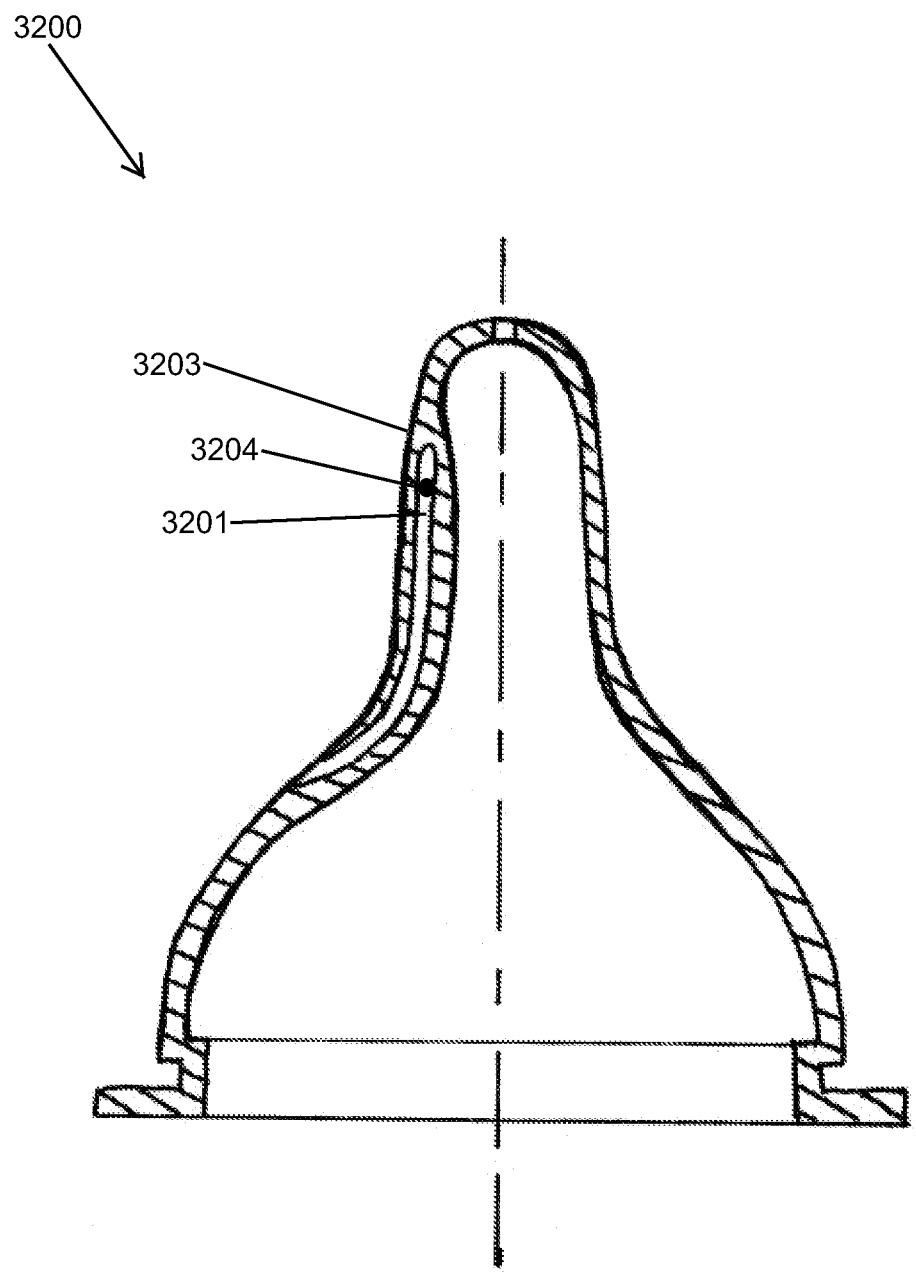
FIGS. 22A, 22B, 22C and 22D illustrate an embodiment of an instrumented nipple.

FIG. 22A shows a cross-section view through an asymmetric nipple 3200, illustrating a tunnel 3201 disposed inside of a thickened sidewall on the hard palate side. A pressure-sensing catheter with a transducer plate 3204 located at the distal end of the catheter 3203 can be inserted into the tunnel 3201. In this configuration, the use of a protective Polyethylene (PE) or Silastic tubing sheath around the pressure-sensing transducer is not required, because it is protected within the tunnel.

Alternatively, the tip of the second tunnel is closer to the base, than the first tunnel shown in FIG. 22A. By comparison, the tip of the tunnel in FIG. 22A is closer to the tip of the nipple.

Figure 22B:
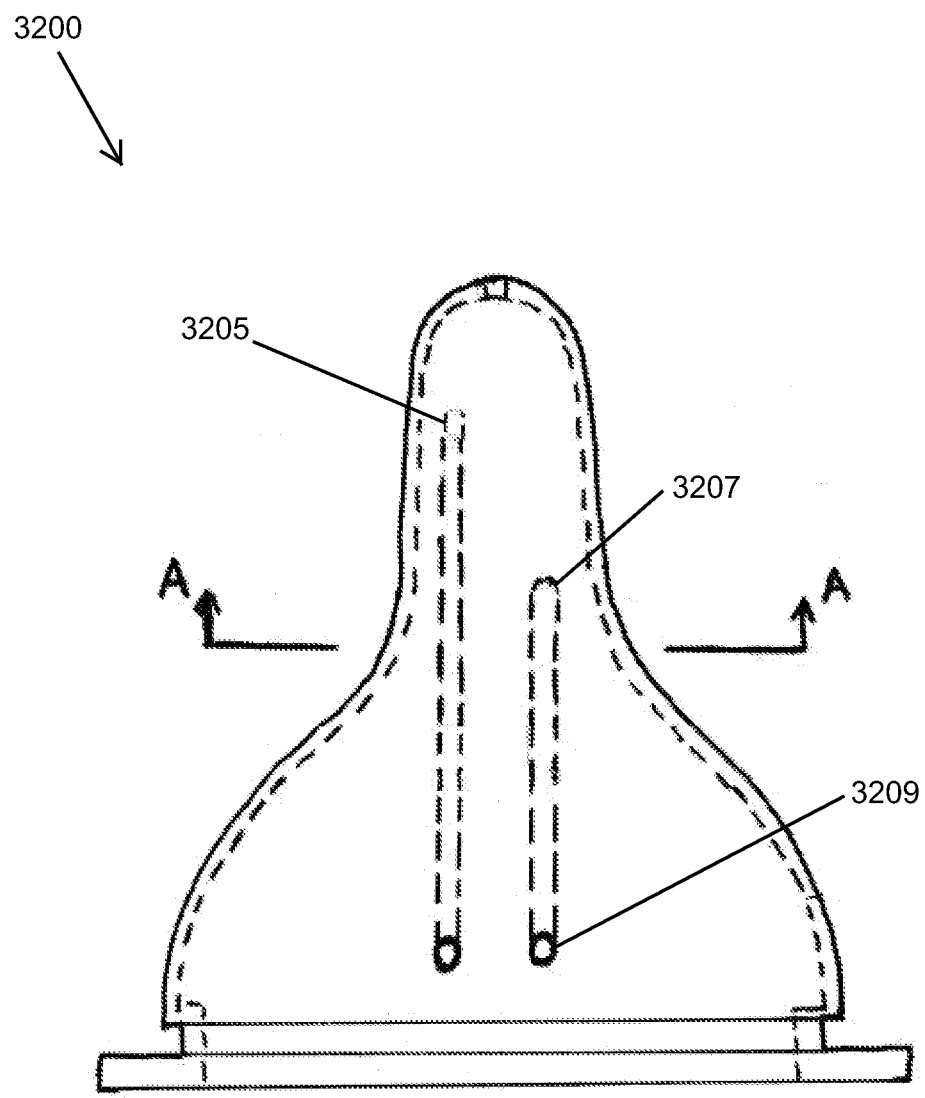

FIG. 22B shows a side view of the asymmetric nipple 3200, with hidden lines indicating the locations of the tunnels 3209 for holding the pair of Expression pressure transducers, $PT_1$ 3205 and $PT_2$ 3207, respectively.

Figure 22C:
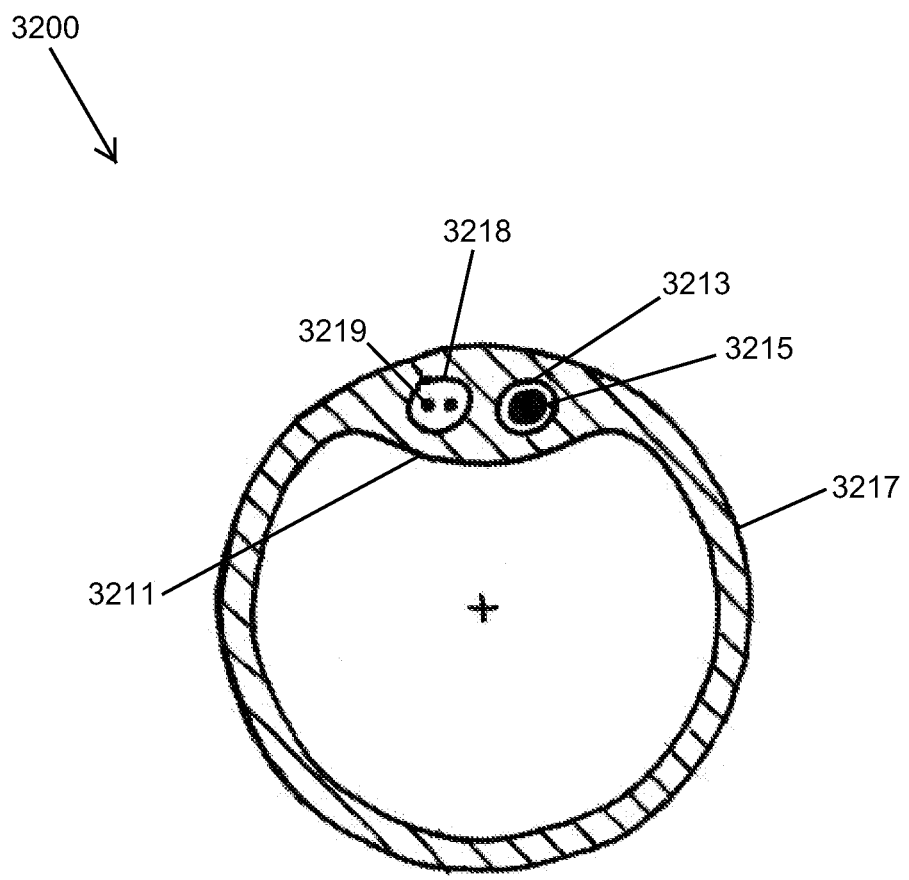

FIG. 22C shows the cross-section 'A-A' of the asymmetric nipple 3200, showing the thickened wall 3211 containing two tunnels (holes) 3213 and 3218. In this example, the tunnel on the left has a pair of signal wires 3219 leading to/from a pressure transducer (e.g., $PT_1$ (not shown)), and the right tunnel containing a pressure transducer head 3215 (e.g., $PT_2$).

Figure 22D:
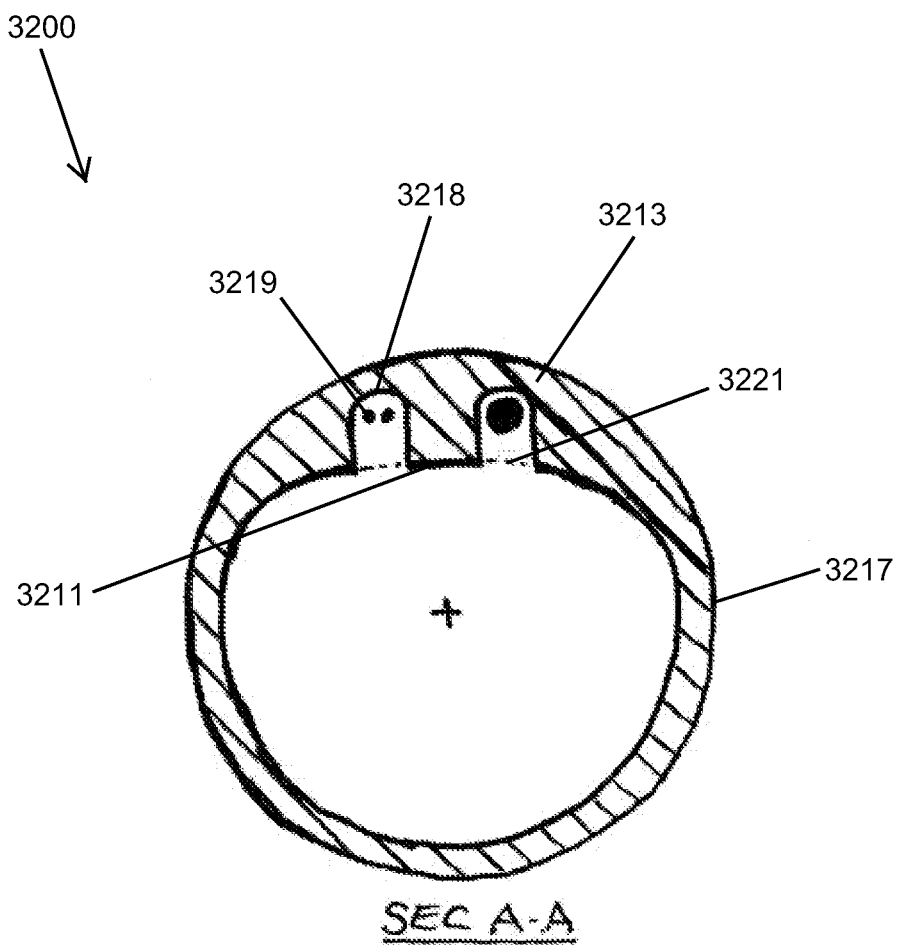

FIG. 22D shows the cross-section 'A-A' of another asymmetric nipple 3200, showing the thickened wall 3211 containing two channels 3218 and 3213. The channel on the left 3218 has a pair of signal wires 3219 leading to/from a pressure transducer (not shown) (e.g., $PT_1$), and the right channel containing a pressure transducer head (e.g., $PT_2$). In this example, the channels are open towards the inside of the nipple. After laying (placing) the catheters inside the open channels, the channels can be closed/secured 3221 by a number of different ways, for example: closing the opening with a piece of tape, or filling/caulking the channel with a flexible adhesive filler material (i.e., silicone).

Alternatively, the channels are open towards the outside of the nipple. After laying (placing) the catheters inside the open channels, the channels can be closed/secured by a number of different ways, for example: closing the opening with a piece of tape, or filling/caulking the channel with a flexible adhesive filler material (i.e., silicone).

Stand-Alone Flow Rate Sensor Module

A second class of flow rate sensors comprise one or more sensing elements contained inside a stand-alone flow rate module that is separate from the nipple, and positioned somewhere in-between the fluid reservoir (i.e., milk bottle) and the nipple. Preferably, the flow rate module can measure, as a function of time, the instantaneous velocity or volumetric (or mass) flow rate of fluid flowing into (or out of) the interior volume/space of the nipple. Since the flow rate module is further removed (2-4 cm) from the nipple tip, the measurement of flow rate (and, hence, bolus volume per suck) is a less-direct measurement. Allowing for changes in the internal volume of the nipple when compressed during Expression, the flow rate module should be able to measure negative fluid velocities (milk travelling in the opposite/backwards direction). Likewise, any numerical integration algorithm used to calculate the bolus volume per suck should be able to account for some period of time during a suck when the fluid velocity may be negative.

The flow rate module can utilize any of the wide variety (presented earlier) of methods, devices, and structures that are capable of measuring properties of a fluid in motion (and, hence, volumetric or mass flow rate), including, but not limited to: pressure differential/drop across a flow discontinuity/restriction (e.g., Venturi, calibrated orifice ($\Delta P$), ultrasonic, thermal flow technique (e.g., RTD thermistor, hot-wire technique), MEMS micromachines, electrochemical techniques (electrolytes, electrical admittance, Lab-on-a-Chip), MEMS Coriolis-effect flowmeter (resonant tube), semiconductor field effect, Particle Image Velocimetry (PIV), and flow-based laser/optical techniques.

A stand-alone flow rate module can have a generally cylindrical shape, and comprises at least one flow channel connecting a back end to a front end, for transferring fluid from the bottle to the nipple. The stand-alone module also comprises a flow rate sensing means for measuring the fluid's velocity and/or flow rate inside the at least one flow channel. The flow channel can have a necked-down or compressed region with a higher fluid velocity, where pressure drop measurements are made. The flow rate module can optionally comprise electronic means for wirelessly transmitting the measured and/or transformed data to a remote receiver (i.e., a laptop computer, a smart phone, or tablet).

Figure 15A:
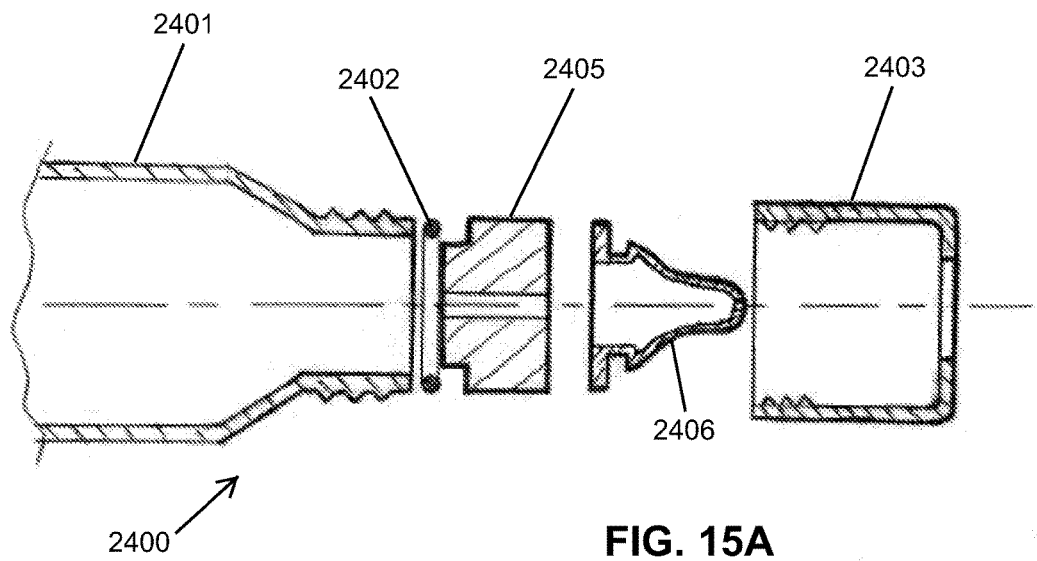
FIGS. 15A and 15B illustrate embodiments of an instrumented nipple.
Figure 15B:
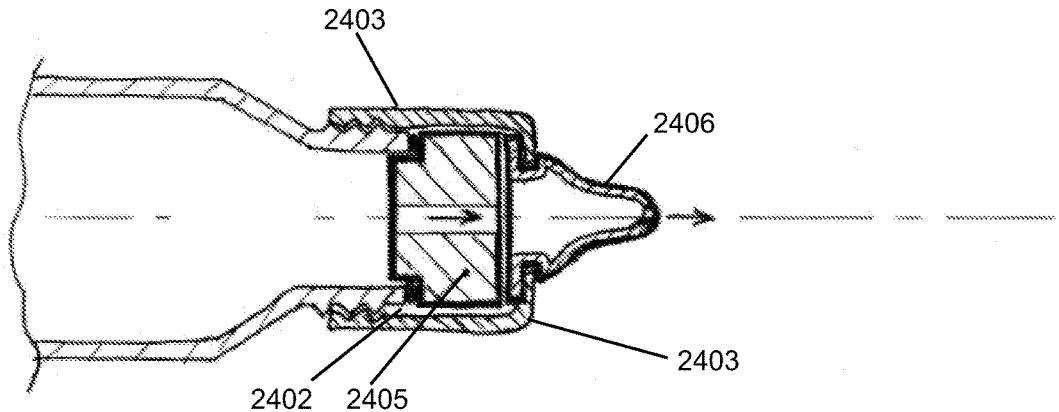

FIG. 15A shows a cross-section, exploded view of an embodiment of a flow rate module for an OMK system, according to the present invention. FIG. 15B shows a cross-section view of the assembled components. An elongated crown ring 2403 screws onto the neck of the bottle 2401, thereby compressing the nipple 2406, the flow rate module 2405, and an O-ring seal 2402, against the flat end of the bottle's neck (FIG. 15B).

Figure 16:
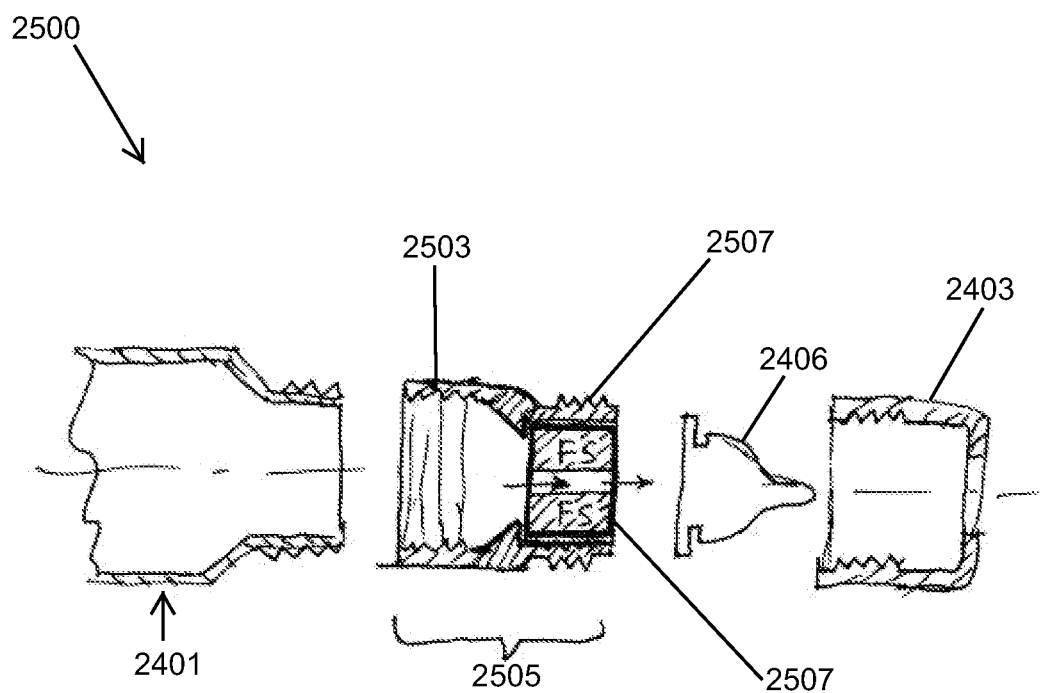
FIG. 16 illustrates an embodiment of an instrumented nipple.

FIG. 16 shows a cross-section, exploded view of another embodiment of a flow rate module for an OMK system 2500. The flow rate module (preferably wireless) 2507, sits inside of transition piece/adaptor 2505 that has internal screw threads 2503 at back end that mates with the bottle 2401, and that has external screw threads 2507 at the front end that mates to the nipple 2406 (held by the crown ring 2403).

Figure 17A:
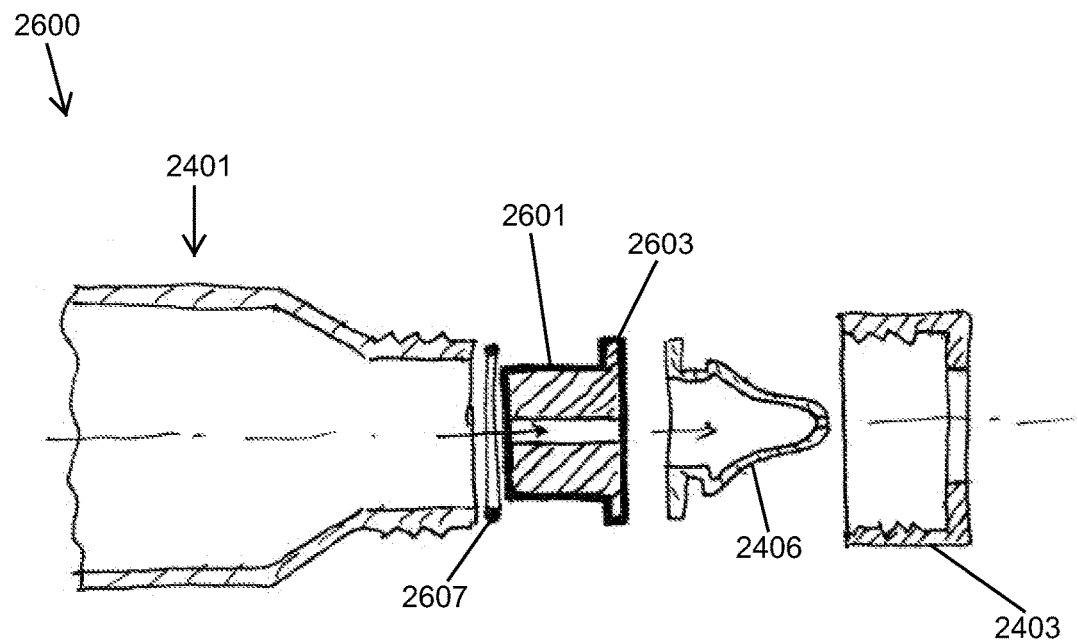
FIGS. 17A and 17B illustrate embodiments of an instrumented nipple.
Figure 17B:
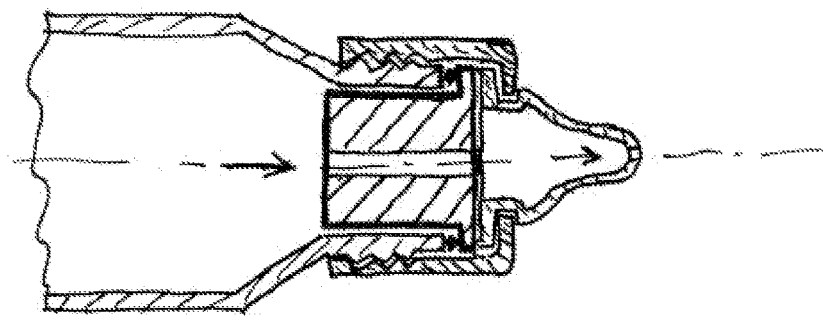

FIG. 17A shows a cross-section, exploded view of another embodiment of a flow rate module for an OMK system 2600. The flow rate module 2601 (preferably wireless) has an integral circular flange 2603 at the front end that mates with the nipple 2406 (held by the crown ring 2403). The flow rate module 2601 itself has a slightly less outer diameter than the inner diameter of the bottle's neck, which allows the flow rate module to slip inside of the bottle's neck. An O-ring seal 2607 is disposed in-between the module's circular flange 2603 and the flat end of the bottle's 2401 neck. FIG. 17B shows the assembled components, which is a very compact assembly.

Alternative Concepts for Measuring Flow Rate

Other techniques can be used, in addition to, or in place of, a stand-alone or nipple-integrated flow rate sensor module or device. For example, the change in weight of liquid inside the reservoir (bottle) can be measured before and after a single suck, to get the bolus volume per suck. Or, the change in height of the liquid column inside the reservoir (bottle) can be measured, with the difference being proportional to the volume (bolus) of liquid lost during a single suck. The change in weight ($\Delta W$) can be measured by using a sensitive pressure transducer at the bottom of the bottle to measure small changes in pressure (weight of the fluid above the pressure transducer) when liquid is removed from the bottle during feeding.

Alternatively, the change in internal air pressure (increase in vacuum level) inside of a sealed bottle (i.e., no one-way, anti-vacuum valve) can be measured with a sensitive pressure transducer placed at or near the top of the bottle. The removal of a bolus of liquid during a single suck creates an incremental change in the vacuum pressure level (via the relationship PV=NRT), which can be measured, in real-time, by the pressure transducer. Once a particular bottle's geometry has been calibrated (and assuming a bottle with a constant cross-section along its length), then the drop in internal air pressure measured by the pressure transducer, in real-time, will correlate directly to the volume of liquid removed, in real-time, from the nipple. This technique was used by Jain, et. al. (18).

Alternatively, the change in height ($\Delta H$) of the liquid column inside the bottle can be measured by a laser beam liquid level sensing system, or by an ultrasonic liquid level sensing system, along with the appropriate electronics and hardware/software data analysis equipment. To get more accurate measurements of change in height of the liquid column, the system can optionally include: 1) an anti-slosh structure inside the bottle (e.g., a bundle of straws or small diameter tubes, or a sponge, which damps unwanted waves/sloshing), and/or 2) a MEMS-based horizontal level detector/indicator mounted to the side of the bottle, for indicating when the bottle is being held vertically (via a buzzing sound, or via LED signal lights, or via a liquid crystal numeric display indicating the bottle's tilt angle in degrees).

Integrated Wireless Instrumentation Module

With the Integrated Chip (IC) technology available today, it is possible to fabricate a compact, miniaturized, integrated wireless instrumentation module (IM) that fits snugly into/inside of the base of a standard nipple, which incorporates an integrated microprocessor, A/D convertors, flow sensor and pressure transducer electronics, battery, transmitter, and antenna.

Figure 18:
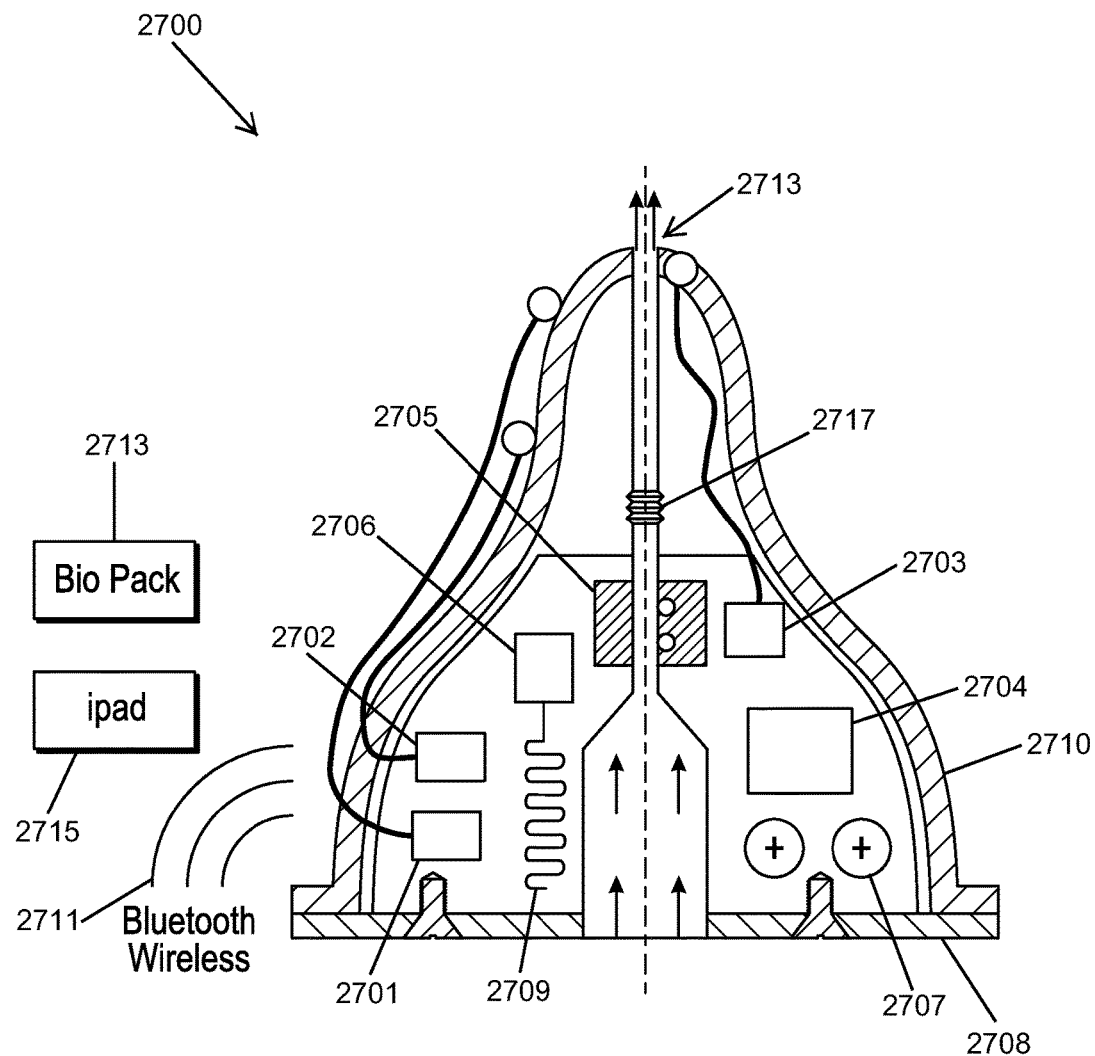
FIG. 18 illustrates an embodiment of an instrumented nipple.

FIG. 18 shows an embodiment of an instrumented nipple 2700 comprising a compact, miniaturized, integrated wireless instrumentation module (IM) that fits snugly into the base of a standard nipple 2710. The wireless IM can comprise one or more of the following instruments: 1) a flow rate sensor 2705, 2) pressure transducer(s) 2701, 2702, 2703 and electrical leads to the module, 3) microprocessor 2704, 4) battery 2707, 5) transmitter 2706, 6) antenna 2709, and 7) mounting plate 2708. The wireless IM can transmit data via, for example, Bluetooth 2711, to a BioPack data collection unit 2713; an iPad 2715; or laptop computer, etc. A flexible metal bellows 2717 can be used to permit flexing (bending) of a tube connecting the flow rate sensor 2705 component with the exit hole at the nipple's tip 2713.

Optical Instrumentation

In some embodiments, an OMK monitoring system can comprise a micro-sized video camera (not shown) (i.e., CCD or CMOS) device mounted at, or near, the nipple tip 2713 for viewing into the infants' mouth. Also, a miniature LED light source (which can be an infrared source) can be mounted at, or near, the nipple's tip for providing illumination of the infant's mouth and oral cavity.

Figure 19:
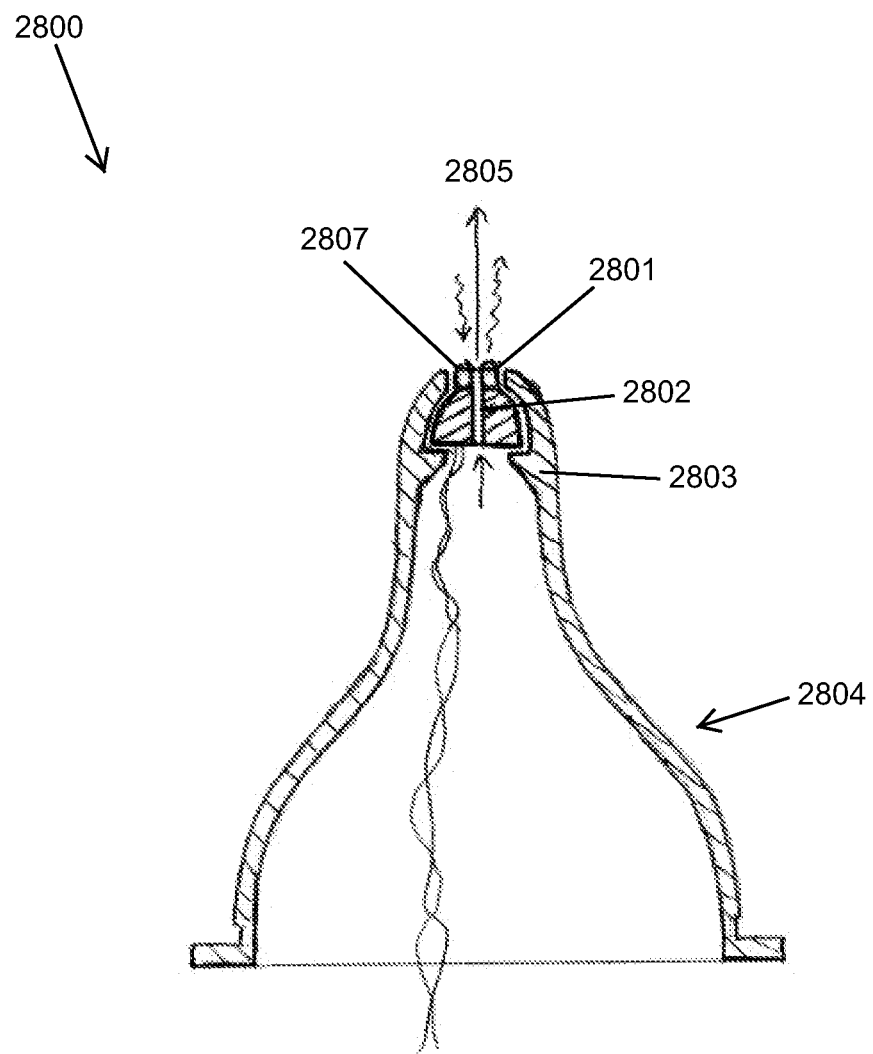
FIG. 19 illustrates an embodiment of an instrumented nipple.

FIG. 19 shows an embodiment of an instrumented nipple for an OMK system 2800, where the LED light source 2801 is integrated/combined with the micro-sized video camera as a single miniature component. The combined video/light component can be held in place, for example, by one or more internal grips (bumps, shoulders, or shelves) 2803 that are integrally molded along with the silicone nipple 2804 as a single, monolithic, unitary body. Optionally, the video camera can detect IR light (in addition to the normal visual light). The combined video/light component can optionally have a central flow channel 2805 for carrying fluid (milk) out through the nipple's tip (which is now enlarged).

Acoustic Instrumentation

In some embodiments, an OMK monitoring system can comprise one or more microphones or acoustic transducers inside and/or outside of the nipple for generating and/or listening to and/or recording acoustic sounds from inside of the nipple or inside of the infant's oral cavity during feeding. Analysis of these sounds may be correlated to the different types of oral feeding techniques (i.e., Suction and Expression), and may be correlated to other sounds (sounds of swallowing or breathing/respiration).

Temperature Instrumentation

In some embodiments, an OMK monitoring system can comprise one or more means for measuring temperature inside and/or outside of the nipple (e.g., inside of the infant's mouth during feeding). The means for measuring temperature can include, for example: thermocouples, thermistors/RTD strips on a substrate, and IR camera/CCD chips.

Figure 20A:
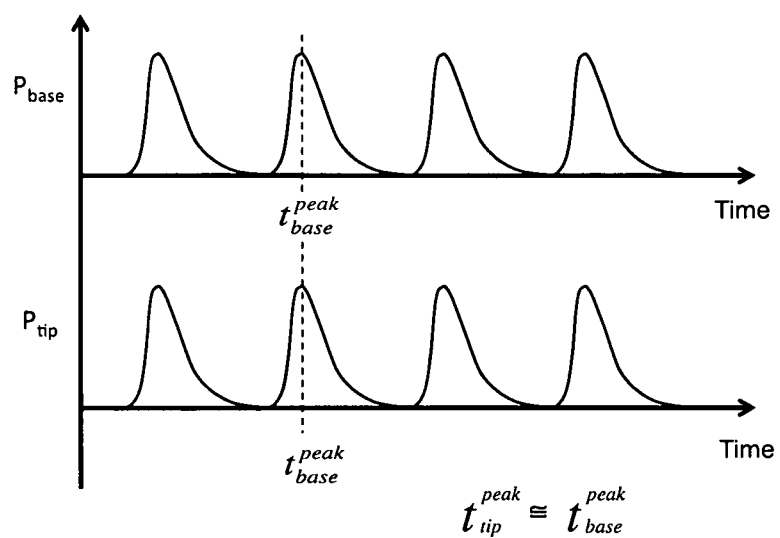
FIGS. 20A and 20B illustrate a representative trace of infant oral motor kinetics as measured with an embodiment of an OMK system.
Figure 20B:
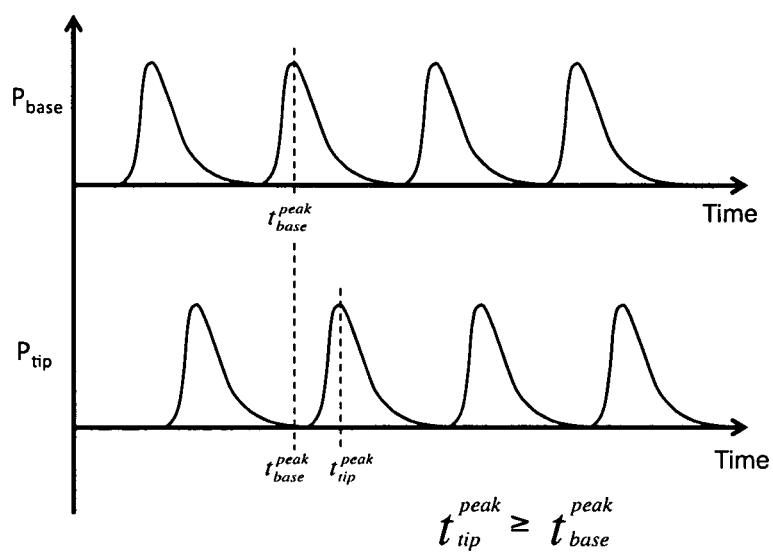

FIGS. 20A and 20B illustrates feeding from an instrumented nipple over time. FIG. 20A illustrates the tpeak base measured from the Ptip and the tpeak base measured from the Pbase illustrates, the compression-only mode of the Expression component of sucking when the peaks align as shown. In contrast FIG. 20B illustrates the "compression plus stripping" mode of the Expression component of sucking when an offset of the tpeak base measured from Ptip when compared to tpeak base of Pbase as shown.

Figure 21:
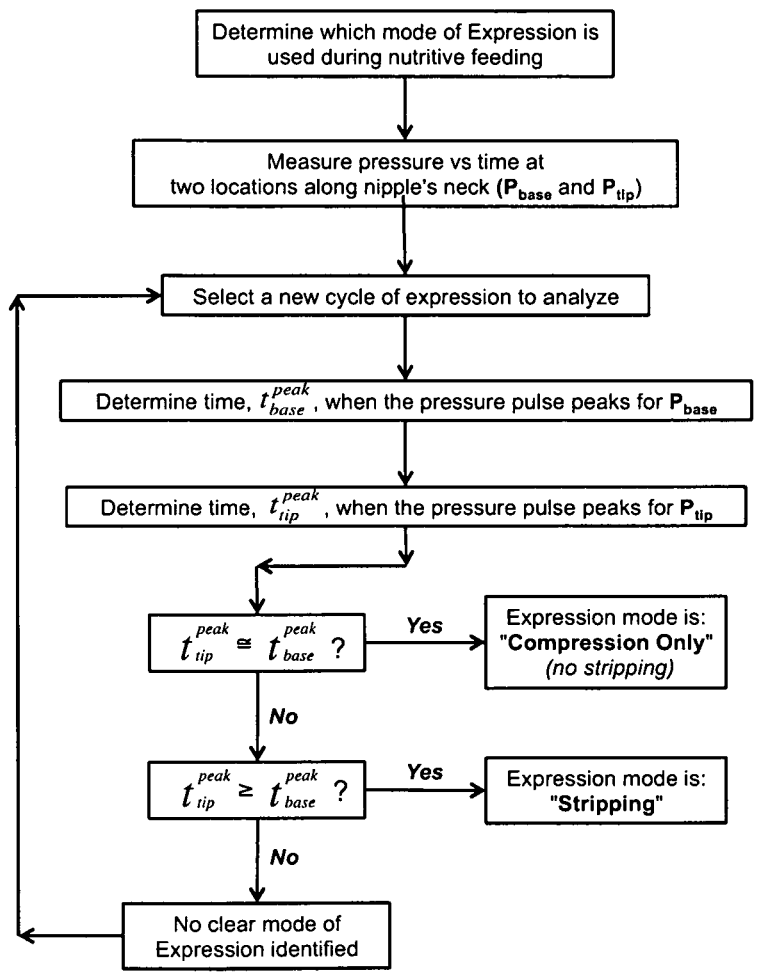
FIG. 21 illustrates a method for determining which mode of Expression is used during feeding as measured with an instrumented nipple.

FIG. 21 illustrates a flow chart used in combination with the OMK system to determine whether the infant is expressing compression only action or stripping action.

Fabrication of Suction Channel

FIG. 1 shows a section of stiff polyethylene (PE) tubing disposed inside of a nipple, going from the base to the tip of the nipple. This section of PE tubing is called the "Suction Channel". A pressure sensor transducer catheter, for measuring the intra-oral Suction pressure, is inserted inside the PE tubing, which serves as a protective sheath/guide for the sensor's signal wires.

An example of a method of fabricating the Suction Channel is as follows. The Suction PE tubing is pre-inserted at the 'factory' in a constant (repeatable) manner using a block template with a pre-formed/pre-cast channel into which the PE tubing will be inserted via a "curved needle", such that the PE tubing will be always in the same position in relation to the inside and outside of the tubing vs. the nipple hole. The PE tubing is inserted with a trocard/wire to maintain patency of PE tubing when the transducer is inserted. At the time of use:

1) Remove trocard/wire;
2) Insert Pressure Sensor transducer;
3) Use blue Luer-lock to tighten in place.

References

The following references are incorporated herein by reference:

1. Wolff, P. H. (1968) The serial organization of sucking in the young infant. Pediatrics 42: 943-956.
2. Jain, L., Sivieri, E., Abbasi, S. & Bhutani, V. K. (1987) Energetics and mechanics of nutritive sucking in the preterm and term neonate. J Pediatr 111: 894-898.
3. deMonterice, D., Meier, P. P., Engstrom, J. L., Crichton, C. L. & Mangurten, H. H. (1992) Concurrent validity of a new instrument for measuring nutritive sucking in preterm infants. Nurs. Res. 41: 342-346.
4. Kron, R. E., Ipsen, J. & Goddard, K. E. (1968) Consistent individual differences in the nutritive sucking behavior of the human newborn. Psychosom. Med 30: 151-161.
5. Mathew, O. P., Clark, M. L., Pronske, M. L., Luna-Solarzano, H. G. & Peterson, M. D. (1985) Breathing pattern and ventilation during oral feeding in term newborn infants. J Pediatr 106: 810-813.
6. Sameroff, A. J. (1968) The components of sucking in the human newborn. J Exp. Child Psychol. 6: 607-623.
7. Dubignon, J. & Campbell, D. (1969) Sucking in the newborn during a feed. J Exp. Child Psychol. 7: 282-298.
8. Lau, C., Sheena, H. R., Shulman, R. J. & Schanler, R. J. (1997) Oral feeding in low birth weight infants. J Pediatr 130: 561-569.
9. Lau, C., Alagugurusamy, R., Schanler, R. J., Smith, E. O. & Shulman, R. J. (2000) Characterization of the developmental stages of sucking in preterm infants during bottle feeding. Acta Paediatr 89: 846-852.
10. Ardran, G. M., Kemp, F. H. & Lind, J. A. (1958) Cineradiographic study of breastfeeding. Br J Radiol 31: 156-162.
11. Ardran, G. M., Kemp, F. H. & Lind, J. (1958) A cineradiographic study of bottle feeding. Br J Radiol 31: 11-22.
12. Fucile, S., Gisel, E. G., McFarland, D. H. & Lau, C. (2011) Oral and non-oral sensorimotor interventions enhance oral feeding performance in preterm infants. Dev. Med. Child Neurol. 53: 829-835.
13. Lau, C. & Smith, E. O. (2011) A Novel Approach to Assess Oral Feeding Skills of Preterm Infants. Neonatology. 100: 64-70.
14. Lau C (2012) Development of oral feeding skills in the preterm infant. In: The Handbook of Growth and Growth Monitoring in Health and Disease, Pt 3 (VR Preedy ed.), pp. 499-512. Springer, New York, N.Y.
15. Lau, C. & Smith, E. (2012) Interventions to Improve the Oral Feeding Performance of Preterm Infants. Acta Paediatr ePrint.
16. Lau C (2012) Is there an advantage for preterm infants to feed orally in an upright or sidelying position? J Neonatal Nursing.
17. Lau, C. & Kusnierczyk, I. (2001) Quantitative evaluation of infant's nonnutritive and nutritive sucking. Dysphagia 16: 58-67.
18. Jain, L., Sivieri, E., Abbasi, S. & Bhutani, V. K. (1987) Energetics and mechanics of nutritive sucking in the preterm and term neonate. J. Pediatr. 111: 894-898.

Wolf L S, Glass R P, Feeding and swallowing disorders in infancy: assessment and management. Tucson: Therapy Skills Builders, 1992.

Arvedson J C, Lefton-Greif M A, Pediatric videofluoroscopic swallow studies. A profession manual with caregiver guidelines. San Antonio: Communication Skill Builders, 1998.

Daniels H, Casaer P, Devlieger H, Eggermont E 1986 Mechanisms of feeding efficiency in preterm infants. J Pediatr Gastroenterol Nutr 5:593-596

Gryborski J 1965 The swallowing mechanism of the neonate. Pediatrics 35:445-452

Lau C, Hurst N 1999 Oral feeding in infants. Curr Probl Pediatr 29:105-124

Lau C, Schanler, R J. Oral feeding in infant: Advantage of a self-paced milk flow. *Acta Paediatr* 2000; 89: 453-9

Simpson C, Schanler R J, Lau C. Early introduction of oral feeding in preterm infants. *Pediatrics* 2002; 110: 517-522

Fucile S, Gisel, E, Lau C. Oral stimulation accelerates the transition from tube to oral feeding in preterm infants. *J Pediatr* 2002; 141: 230-236

Lau C, Smith E O, Schanler R J. Coordination of suck-swallow and swallow-respiration in preterm infants. *Acta Paediatr* 2003; 92:721-7

Fucile S, Gisel E, Lau C. Effect of an oral stimulation program on the maturation of sucking skills of preterm infants. Dev Med Child Neurol, 2005; 47: 158-62

Scheel C E, Schanler R J, Lau C. Does the choice of bottle nipple affect the oral feeding performance of very-low-birth-weight (VLBW) infants? *Acta Physiologica*, 2005; 94: 1266-72

Amaizu N, Shulman R J, Schanler R J, Lau C. Maturation of oral feeding skills in very low birth weight infants. *Acta Paediatr* 2008, 97: 61-7

Fucile S, Gisel E, Schanler R J; Lau C. A vacuum-free bottle enhances preterm infants' nutritive sucking skills. *Dysphagia* 2009, 24:145-51 (DOI 10.1007/s00455-008-9182-z)

Rasch S, Sangild P T, Gregersen H, Schmidt M, Oman T, Lau C. The preterm piglet—a model in the study of esophageal development in preterm neonates *Acta Paediatrica* 2010, 99: 201-8 (DOI:10.1111/j.1651-2227.2009.01564.x)

Fucile S, McFarland DH, Gisel EG, Lau C. Oral and nonoral sensorimotor interventions facilitate suck-swallow-respiration functions and their coordination in preterm infants. *Dysphagia. Early Human Dev* 2012; 88:345-550 (doi: 10.1016/j.earthhumdev.2011.09.007).

What is claimed is:

1. An instrumented nipple for monitoring oral motor kinetics in an infant comprising:
    an instrumented nipple comprising a first pressure transducer and a second pressure transducer for detecting pressure pulses when the nipple is placed in the mouth of an infant; and
    a processor in operational communication with the first pressure transducer and the second pressure transducer of the nipple for processing signals from the first pressure transducer and the second pressure transducer to provide information about the infant's oral motor kinetics when the nipple is in the infant's mouth;
    wherein the first and second pressure transducers are mounted on a same outside surface of the nipple, and are spaced apart from each other by a distance $L_0$ along the nipple's long axis; and
    wherein the first pressure transducer and the second pressure transducer are located within one or more flexible tubes positioned at least partially on the exterior of a neck of the nipple.

2. The system of claim 1 wherein the first pressure transducer and second pressure transducer measure the positive pressures exerted by an Expression component of sucking when the infant's tongue compresses and/or strips the nipple against an infant's hard palate.

3. The system of claim 1 wherein the second pressure transducer is located closer to a base of the nipple as compared to the position of the first pressure transducer which is located closer to a tip of the nipple as compared to the position of the second pressure transducer.

4. The system of claim 1 wherein the distance $L_0$, between the first pressure transducer and the second pressure transducer is between about 0.1-3 cm along the long axis of the nipple.

5. The system of claim 1 wherein the nipple is selected from the group consisting of a nipple shield, a finger of a glove, a pacifier, and a nipple of a feeding bottle.

6. The system of claim 1 wherein the processing by the processor is selected from the group consisting of receiving, storing, displaying, analyzing and transmitting.

7. An instrumented nipple comprising:
a first pressure transducer and a second pressure transducer associated with the instrumented nipple for detecting pressure pulses when the instrumented nipple is placed in the mouth of an infant;
wherein the first and second pressure transducers are mounted on a same outside surface of the nipple, and are spaced apart from each other by a distance $L_0$ along the nipple's long axis; and
wherein the first and second pressure transducers are located within one or more flexible tubes positioned at least partially on the exterior of a neck of the nipple.

8. The instrumented nipple of claim 7 wherein the nipple is selected from the group consisting of a nipple shield, a finger of a glove, a pacifier, and a nipple of a feeding bottle.

9. The instrumented nipple of claim 7 wherein the first and second pressure transducers are located within one or more flexible tubes positioned at least partially on the exterior of a neck of the nipple.

10. The instrumented nipple of claim 7 wherein the distance $L_0$, between the first pressure transducer and the second pressure transducer is between about 0.1-3 cm along the long axis of the nipple.

11. A method for evaluating an infant's oral motor kinetics comprising:
a) inserting an instrumented nipple into a mouth of an infant; wherein the instrumented nipple comprises a nipple comprising a first pressure transducer and a second pressure transducer for detecting pressure pulses when the nipple is placed in the mouth of the infant; and wherein the first and second pressure transducers are mounted on a same outside surface of the nipple, and are spaced apart from each other by a distance $L_0$ along the nipple's long axis; and wherein the first pressure transducer and the second pressure transducer are located within one or more flexible tubes positioned at least partially on the exterior of a neck of the nipple;
b) activating the first and second pressure transducers of the instrumented nipple with pressure provided by the infant's tongue pressing against the nipple; and
c) analyzing temporal signals received from activation of the first and second pressure transducers to determine the oral motor kinetics of the infant during sucking; and
d) processing with a processor in operational communication with the first pressure transducer and the second pressure transducer signals from the first pressure transducer and the second pressure pressure transducer to provide information about the infant's oral motor kinetics.

12. The method of claim 11 wherein analyzing the signals includes measuring over time a temporal sequence of pressure pulses generated at the first and second pressure transducers; and determining if a mode of Expression comprises Compression or Stripping.

13. The method of claim 11 wherein the instrumented nipple comprises a finger glove or a pacifier.

14. The method of claim 11 wherein the instrumented nipple comprises a nipple attached to a feeding bottle; and the method further comprises delivering fluid from the bottle to the infant through said instrumented nipple when the infant is feeding.

15. The method of claim 11 further comprising monitoring an amount of fluid delivered to the infant from the nipple during oral feeding.

16. A method for evaluating an infant's oral motor kinetics comprising:
a) inserting an instrumented nipple into a mouth of an infant;
wherein the instrumented nipple comprises: a nipple comprising a first pressure transducer and a second pressure transducer for detecting pressure pulses when the nipple is placed in the mouth of the infant, wherein the first and second pressure transducers are mounted on a same outside surface of the nipple, and are spaced apart from each other by a distance $L_0$ along the nipple's long axis; and
wherein the second pressure transducer is located closer to a base of the nipple as compared to a position of the first pressure transducer, which is located closer to a tip of the nipple as compared to a position of the second pressure transducer;
b) activating the first and second pressure transducers of the instrumented nipple with pressure provided by the infant's tongue pressing against the nipple; and
c) analyzing temporal signals received from activation of the first and second pressure transducers to determine the oral motor kinetics of the infant during sucking; and
d) processing with a processor in operational communication with the first pressure transducer and the second pressure transducer signals from the first pressure transducer and the second pressure transducer to provide information about the infant's oral motor kinetics;
wherein analyzing the signals includes measuring over time a temporal sequence of pressure pulses generated at the first and second pressure transducers; and determining if a mode of Expression comprises Compression or Stripping; and
further comprising analyzing the Expression component of sucking with the instrumented nipple to identify compression and/or stripping signals by comparing the temporal synchrony of peak (maximum) pressure pulses measured by the first pressure transducer ($PT_1=PT_{tip}$) and the second pressure transducer ($PT_2=PT_{base}$) according to the following algorithm:
Step 1: determine a tpeak/tip at which the peak pressure occurs for the first pressure transducer at the tip;
Step 2: determine a time, tpeak/base at which the peak pressure occurs for the second pressure transducer at the base, during Step 1;
Step 3: compare $t_{tip}^{peak}$ to $t_{base}^{peak}$;
Step 4: if $t_{base}^{peak} < t_{tip}^{peak}$ then identify the expression mode as "Stripping"; and Step 5: if $t_{tip}^{peak} \cong t_{base}^{peak}$ then identify the expression mode as "Compression Only";

Step 6: if $t_{tip}^{peak} > t_{base}^{peak}$ then identify the expression mode as "No Clear Mode of Expression Identified".

17. The method of claim 16 further comprising monitoring a clinical parameter selected from the group consisting of heart rate, oxygen saturation, respiration, and esophageal activity, and combinations thereof.

18. The method of claim 16, wherein the nipple further comprises a third pressure transducer mounted flush with the nipple wall and located near the distal tip of the nipple; and wherein the method further comprises measuring an intraoral pressure outside of the nipple with the third pressure transducer.

19. The method of claim 16, wherein the first pressure transducer and the second pressure transducer are located within one or more flexible tubes positioned at least partially on the exterior of a neck of the nipple.

20. The method of claim 16, wherein the distance $L_0$, between the first pressure transducer and the second pressure transducer is between about 0.1-3cm along the long axis of the nipple.

21. The method of claim 16, wherein the nipple is selected from the group consisting of a nipple shield, a finger of a glove, a pacifier, and a nipple of a feeding bottle.

22. The method of claim 16, wherein the operational communication of the processor to the pressure transducers is wireless.

23. The method of claim 16 further comprising measuring one or more characteristics of sucking selected from the group consisting of: duration of the sucking action, peak amplitude of the Suction and Expression components of the sucking action, duration of the individual Suction and Expression components of sucking, and number of Suction and Expression events per sucking burst.

* * * * *